(12) United States Patent
Domschke et al.

(10) Patent No.: US 8,324,256 B2
(45) Date of Patent: Dec. 4, 2012

(54) TRI-FUNCTIONAL UV-ABSORBING COMPOUNDS AND USE THEREOF

(75) Inventors: Angelika Maria Domschke, Duluth, GA (US); Lynn Cook Winterton, Alpharetta, GA (US); Troy Vernon Holland, Suwanee, GA (US); Richard Charles Turek, Atlanta, GA (US)

(73) Assignee: Novartis AG, Basel (CH)

( * ) Notice: Subject to any disclaimer, the term of this patent is extended or adjusted under 35 U.S.C. 154(b) by 344 days.

(21) Appl. No.: 12/640,019

(22) Filed: Dec. 17, 2009

(65) Prior Publication Data
US 2010/0168359 A1    Jul. 1, 2010

Related U.S. Application Data

(60) Provisional application No. 61/141,265, filed on Dec. 30, 2008.

(51) Int. Cl.
*A61K 31/41* (2006.01)
*C07D 249/20* (2006.01)
(52) U.S. Cl. ........................ 514/359; 548/257
(58) Field of Classification Search ............... None
See application file for complete search history.

(56) References Cited

U.S. PATENT DOCUMENTS

| | | | |
|---|---|---|---|
| 2,980,646 A * | 4/1961 | Lappin | 524/291 |
| 3,159,646 A | 12/1964 | Milionis | |
| 3,408,429 A | 10/1968 | Wichterle | |
| 3,761,272 A | 9/1973 | Mannens | |
| 4,136,250 A | 1/1979 | Mueller | |
| 4,153,641 A | 5/1979 | Deichert | |
| 4,182,822 A | 1/1980 | Chang | |
| 4,189,546 A | 2/1980 | Deichert | |
| 4,254,248 A | 3/1981 | Friends | |
| 4,259,467 A | 3/1981 | Keogh | |
| 4,260,725 A | 4/1981 | Keogh | |
| 4,261,875 A | 4/1981 | LeBoeuf | |
| 4,276,402 A | 6/1981 | Chromecek | |
| 4,304,895 A | 12/1981 | Loshaek | |
| 4,327,203 A | 4/1982 | Deichert | |
| 4,341,889 A | 7/1982 | Deichert | |
| 4,343,927 A | 8/1982 | Chang | |
| 4,347,198 A | 8/1982 | Ohkada | |
| 4,355,147 A | 10/1982 | Deichert | |
| 4,444,711 A | 4/1984 | Schad | |
| 4,460,534 A | 7/1984 | Boehm | |
| 4,486,577 A | 12/1984 | Mueller | |
| 4,528,311 A | 7/1985 | Beard | |
| 4,543,398 A | 9/1985 | Bany | |
| 4,605,712 A | 8/1986 | Mueller | |
| 4,661,575 A | 4/1987 | Tom | |
| 4,684,538 A | 8/1987 | Klemarczyk | |
| 4,703,097 A | 10/1987 | Wingler | |
| 4,716,234 A | 12/1987 | Dunks | |
| 4,719,248 A | 1/1988 | Bambury | |
| 4,833,218 A | 5/1989 | Lee | |
| 4,837,289 A | 6/1989 | Mueller | |
| 4,954,586 A | 9/1990 | Toyoshima | |
| 4,954,587 A | 9/1990 | Mueller | |
| 5,010,141 A | 4/1991 | Mueller | |
| 5,034,461 A | 7/1991 | Lai | |
| 5,039,761 A | 8/1991 | Ono | |
| 5,070,170 A | 12/1991 | Robertson | |
| 5,079,319 A | 1/1992 | Mueller | |
| 5,164,462 A | 11/1992 | Yang | |
| 5,224,957 A | 7/1993 | Gasser | |
| 5,346,946 A | 9/1994 | Yokoyama | |
| 5,352,753 A | 10/1994 | Yang | |
| 5,358,995 A | 10/1994 | Lai | |
| 5,387,632 A | 2/1995 | Lai | |
| 5,416,132 A | 5/1995 | Yokoyama | |
| 5,451,617 A | 9/1995 | Lai | |
| 5,466,768 A | 11/1995 | Yang | |
| 5,486,579 A | 1/1996 | Lai | |
| 5,489,474 A | 2/1996 | Shinoda | |
| 5,508,317 A | 4/1996 | Müller | |
| 5,554,663 A | 9/1996 | Desobry | |
| 5,559,163 A | 9/1996 | Dawson | |
| 5,583,163 A | 12/1996 | Müller | |
| 5,597,854 A | 1/1997 | Birbaum | |
| 5,663,288 A | 9/1997 | Shinoda | |
| 5,665,840 A | 9/1997 | Pohlmann | |
| 5,712,356 A | 1/1998 | Bothe | |
| 5,723,512 A | 3/1998 | Leppard | |
| 5,760,100 A | 6/1998 | Nicolson | |
| 5,767,169 A | 6/1998 | Leppard | |
| 5,789,464 A | 8/1998 | Müller | |
| 5,843,346 A | 12/1998 | Morrill | |
| 5,849,810 A | 12/1998 | Müller | |
| 5,849,841 A | 12/1998 | Mühlebach | |
| 5,894,002 A | 4/1999 | Boneberger | |
| 5,914,355 A | 6/1999 | Kunzler | |
| 5,936,052 A | 8/1999 | Bothe | |
| 5,945,465 A | 8/1999 | Ozark | |
| 5,962,548 A | 10/1999 | Vanderlaan | |
| 5,965,776 A | 10/1999 | Leppard | |
| 5,981,675 A | 11/1999 | Valint, Jr. | |
| 5,989,462 A | 11/1999 | Buazza | |
| 6,015,842 A | 1/2000 | LeBoeuf | |
| 6,020,528 A | 2/2000 | Leppard | |
| 6,039,913 A | 3/2000 | Hirt | |
| 6,136,880 A | 10/2000 | Snowwhite | |
| 6,153,760 A | 11/2000 | Künzler | |
| 6,165,408 A | 12/2000 | Steinmann | |
| 6,218,463 B1 | 4/2001 | Molock | |

(Continued)

FOREIGN PATENT DOCUMENTS

JP    2007-297469    * 11/2007

(Continued)

*Primary Examiner* — Noble Jarrell
(74) *Attorney, Agent, or Firm* — Jian Zhou

(57) ABSTRACT

Described herein are tri-functional compounds useful in the production of ophthalmic lenses. The compounds are composed of UV absorber having a polymerization initiator directly or indirectly bonded to the ultraviolet absorber, and an olefinic group directly or indirectly bonded to the ultraviolet absorber. Also described herein are polymers and ophthalmic lenses produced from the tri-functional compounds described herein.

16 Claims, 16 Drawing Sheets

U.S. PATENT DOCUMENTS

| | | |
|---|---|---|
| 6,221,303 B1 | 4/2001 | Steinmann |
| 6,244,707 B1 | 6/2001 | Faubl |
| 6,284,813 B1 | 9/2001 | Leppard |
| 6,303,687 B1 | 10/2001 | Müller |
| 6,342,570 B1 | 1/2002 | Bothe |
| 6,359,024 B2 | 3/2002 | Lai |
| 6,359,025 B1 | 3/2002 | Snowwhite |
| 6,361,925 B1 | 3/2002 | Leppard |
| 6,465,538 B2 | 10/2002 | Lai |
| 6,472,489 B1 | 10/2002 | Stockinger |
| 6,479,587 B1 | 11/2002 | Stockinger |
| 6,492,478 B1 | 12/2002 | Steinmann |
| 6,627,124 B1 | 9/2003 | Herbrechtsmeier |
| 6,762,264 B2 | 7/2004 | Künzler |
| 6,776,934 B2 | 8/2004 | Lai |
| 6,914,086 B2 | 7/2005 | Hong |
| 7,052,131 B2 | 5/2006 | McCabe |
| 7,091,283 B2 | 8/2006 | Müller |
| 7,119,210 B2 | 10/2006 | Schlueter |
| 7,238,750 B2 | 7/2007 | Müller |
| 7,268,189 B2 | 9/2007 | Müller |
| 7,381,762 B2 | 6/2008 | Xia |
| 7,396,942 B2 | 7/2008 | Schuleter |
| 7,521,519 B1 | 4/2009 | Hirt |
| 7,541,407 B2 | 6/2009 | Murdaugh, Sr. |
| 7,649,058 B2 | 1/2010 | McCabe |
| 2002/0042022 A1 | 4/2002 | Leppard |
| 2003/0125498 A1 | 7/2003 | McCabe |
| 2004/0082680 A1 | 4/2004 | Phelan |
| 2005/0113549 A1 | 5/2005 | Devlin |
| 2006/0007391 A1 | 1/2006 | McCabe |
| 2006/0252850 A1 | 11/2006 | Jani |
| 2007/0078196 A1 | 4/2007 | Schuleter |
| 2008/0015315 A1 | 1/2008 | Chang |
| 2008/0143003 A1 | 6/2008 | Phelan |
| 2008/0143958 A1 | 6/2008 | Medina |
| 2008/0221675 A1 | 9/2008 | Schlueter |
| 2008/0231798 A1 | 9/2008 | Zhou |
| 2008/0234457 A1 | 9/2008 | Zhou |

FOREIGN PATENT DOCUMENTS

| | | |
|---|---|---|
| WO | 96/28762 A1 | 9/1996 |

* cited by examiner

TRI-FUNCTIONAL UV-ABSORBING COMPOUNDS AND USE THEREOF

This application claims the benefit under 35 U.S.C. §119 (e) of U.S. provisional application Ser. No. 61/141,265 filed on Dec. 30, 2008, herein incorporated by reference in its entirety.

This invention is related to a class of compounds useful for making ophthalmic lenses (including contact lenses and intraocular lenses) capable of blocking ultra-violet ("UV") radiation and thereby protecting corneal to some extent from damages caused by UV radiation. This invention also provides UV-absorbing ophthalmic lenses and methods for making UV-absorbing ophthalmic lenses.

BACKGROUND

In general, contact lenses are produced in mass by a so-called cast-molding process, which involves thermo- or UV-photo-induced free-radical polymerization of a lens-forming composition including vinylic monomers and/or vinylic macromers in molds. UV photo-induced polymerization process is generally preferred because its processing cycle is shorter than the thermo-induced polymerization process. In certain applications, it is desirable to incorporate UV absorbers into the ophthalmic lens. One approach is to copolymerize a polymerizable UV absorber with the other lens-forming vinylic monomers and/or macromer so that the UV absorber is covalently attached to the copolymer. Copolymerizable benzotriazole, benzophenone and triazine UV absorbers, which include an ethylenically unsaturated group covalently linked to their UV-absorbing moieties, are known and have been used previously. However, there are several disadvantages associated with use of a known polymerizable UV-absorber. First, the efficiency of incorporation of the UV-absorber in lenses may not be certain. Further, a UV-absorber present in a lens forming composition can reduce the amount of UV radiation available to initiate polymerization and may even lower the efficiency of covalent incorporation of the UV absorber into resultant lenses. Unreacted UV absorbers generally must be removed from the lenses in one or more extraction processes. Second, a UV-absorber may result in ineffective or uneven photo-polymerization of the lens forming composition.

Therefore, it would be desirable to have a new UV-absorbing compound that has a relatively high efficiency of incorporation and minimal adverse effect on the UV photo-polymerization of lens forming compositions.

SUMMARY

Described herein are tri-functional compounds useful in the production of UV-blocking (or UV-absorbing) ophthalmic lenses. The compounds are composed of a UV absorbing moiety, a polymerization initiator moiety directly or indirectly bonded to the UV absorbing moiety, and an olefinically (or ethylenically) unsaturated group directly or indirectly bonded to the UV-absorbing moiety and capable of undergoing polymerization with other lens-forming materials (e.g., ethylenically unsaturated compounds). In preferred embodiments, the compounds do not necessarily interfere with the polymerization of lens-forming materials upon curing. Also described herein are polymers and ophthalmic lenses produced from the tri-functional compounds described herein as well as methods for making UV-absorbing ophthalmic lenses by using a tri functional UV-absorbing compound of the invention. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
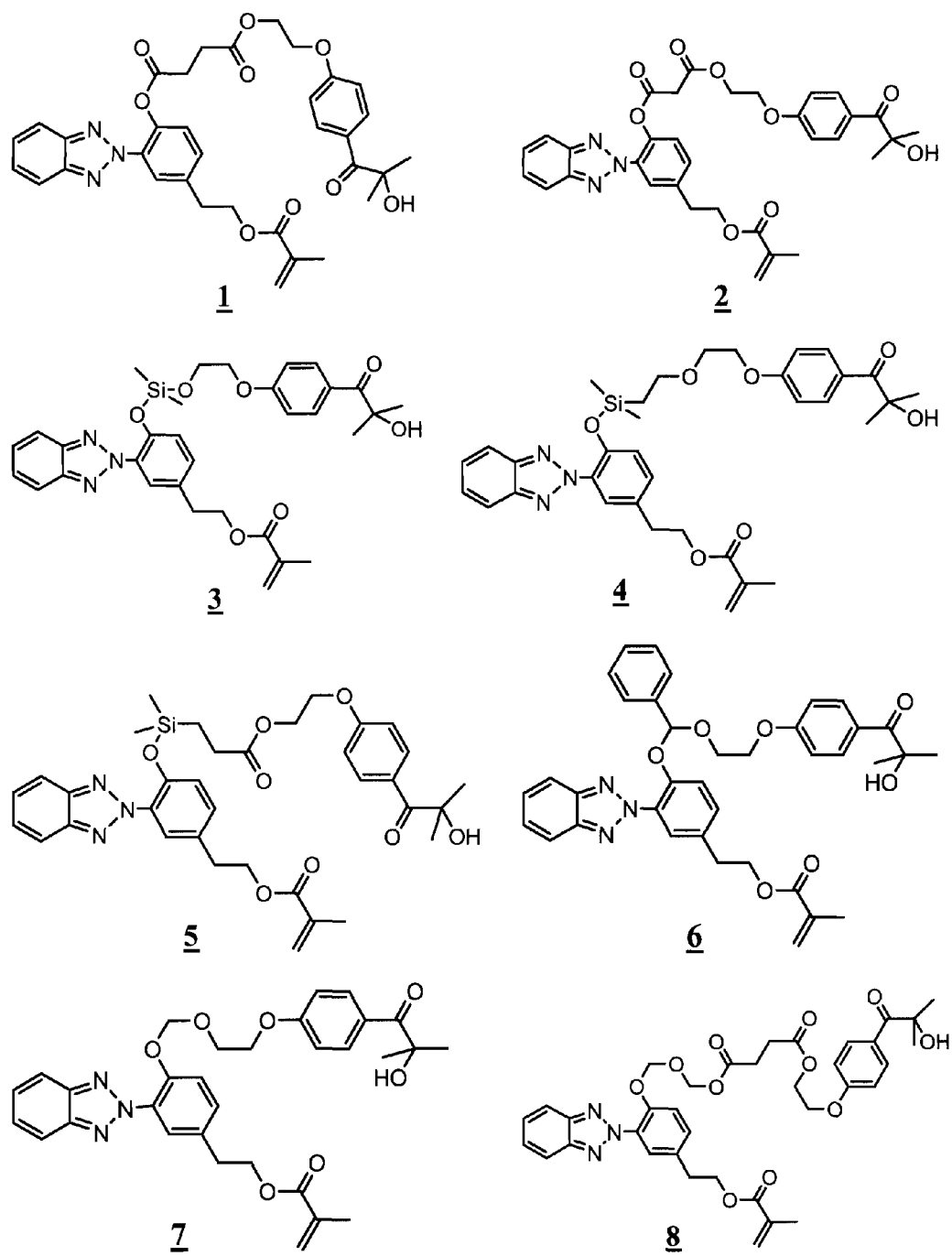
FIG. 1 shows the structures of some preferred tri-functional compounds of the invention.
Figure 1:
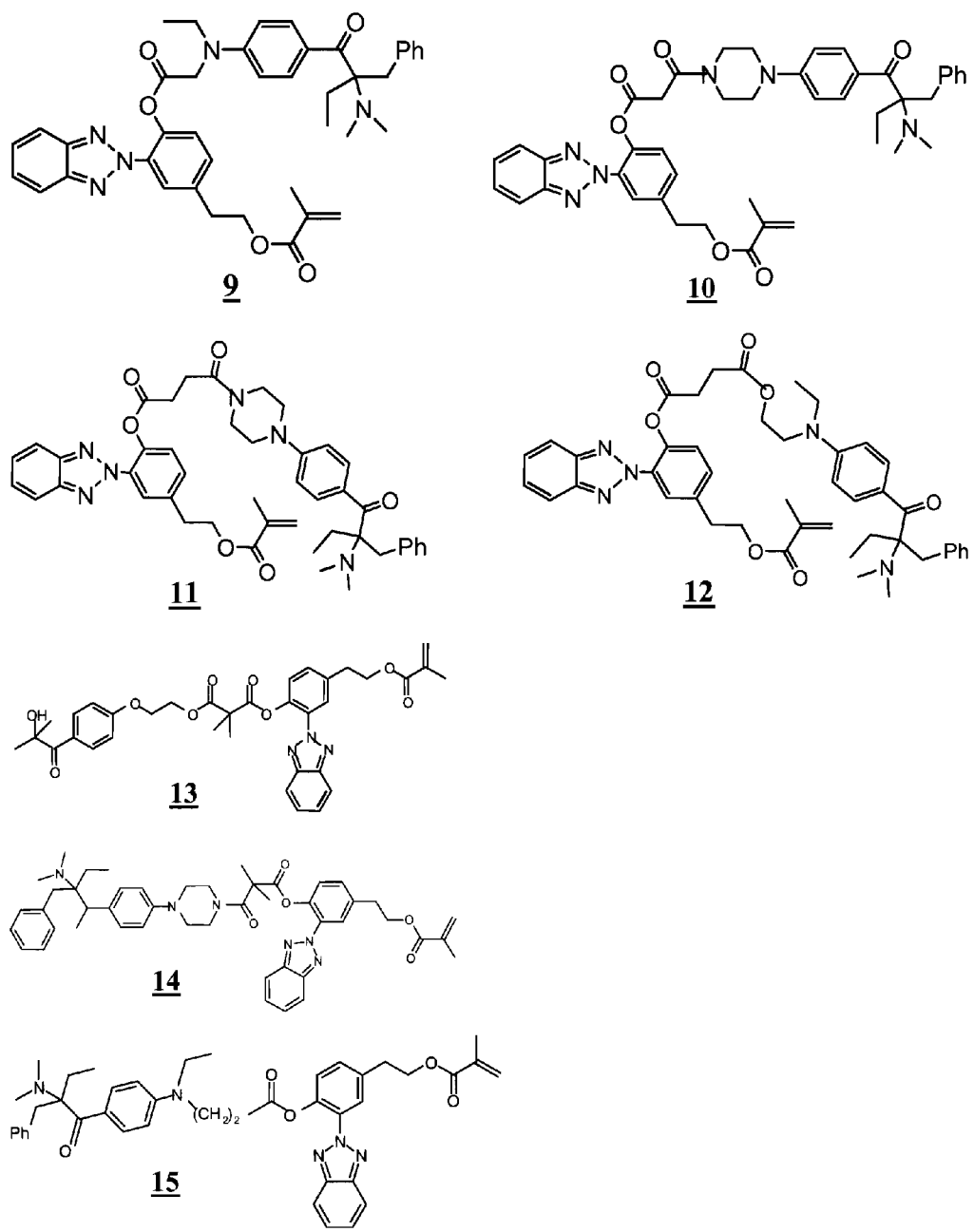
Figure 1:
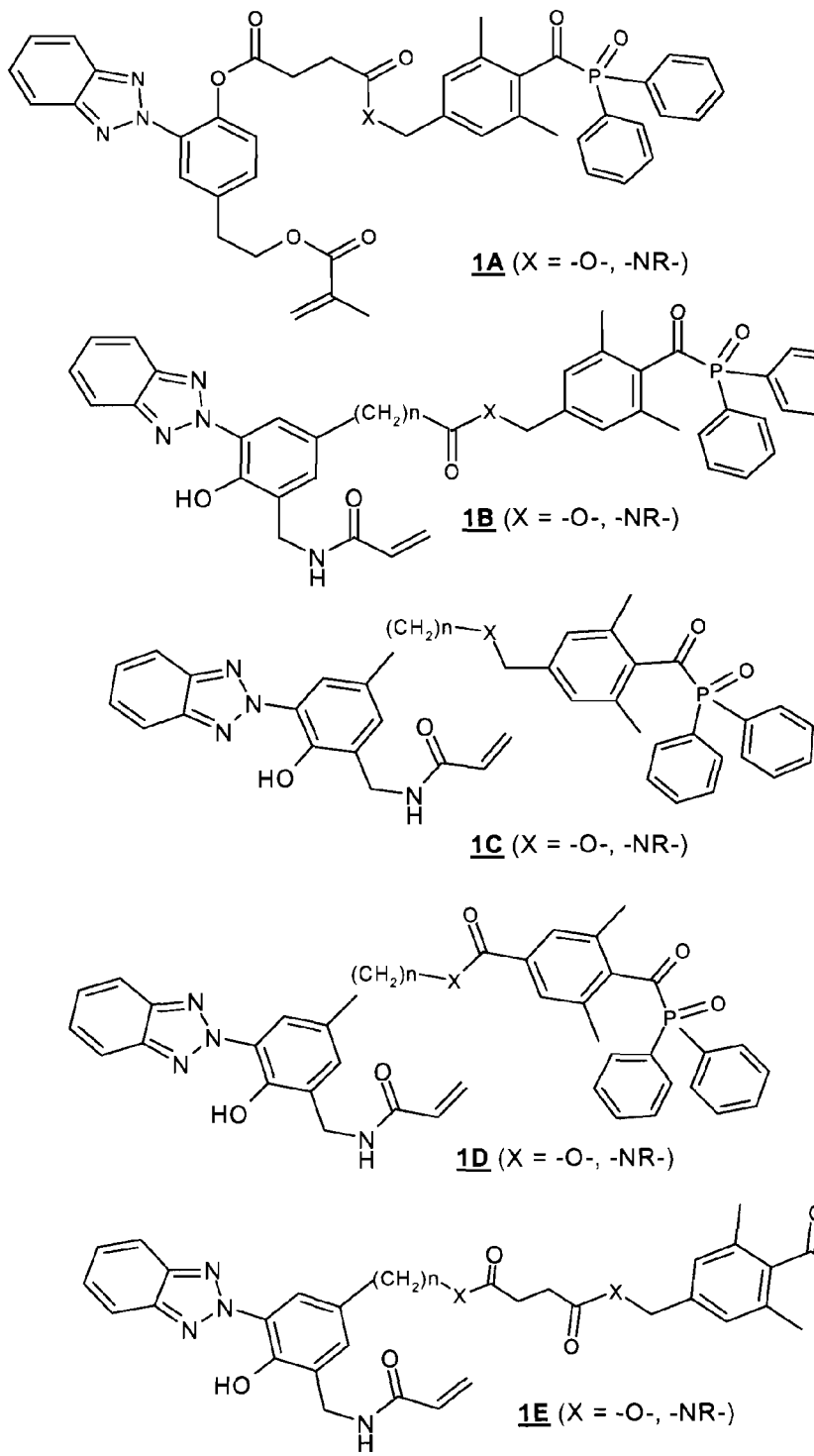
Figure 1:
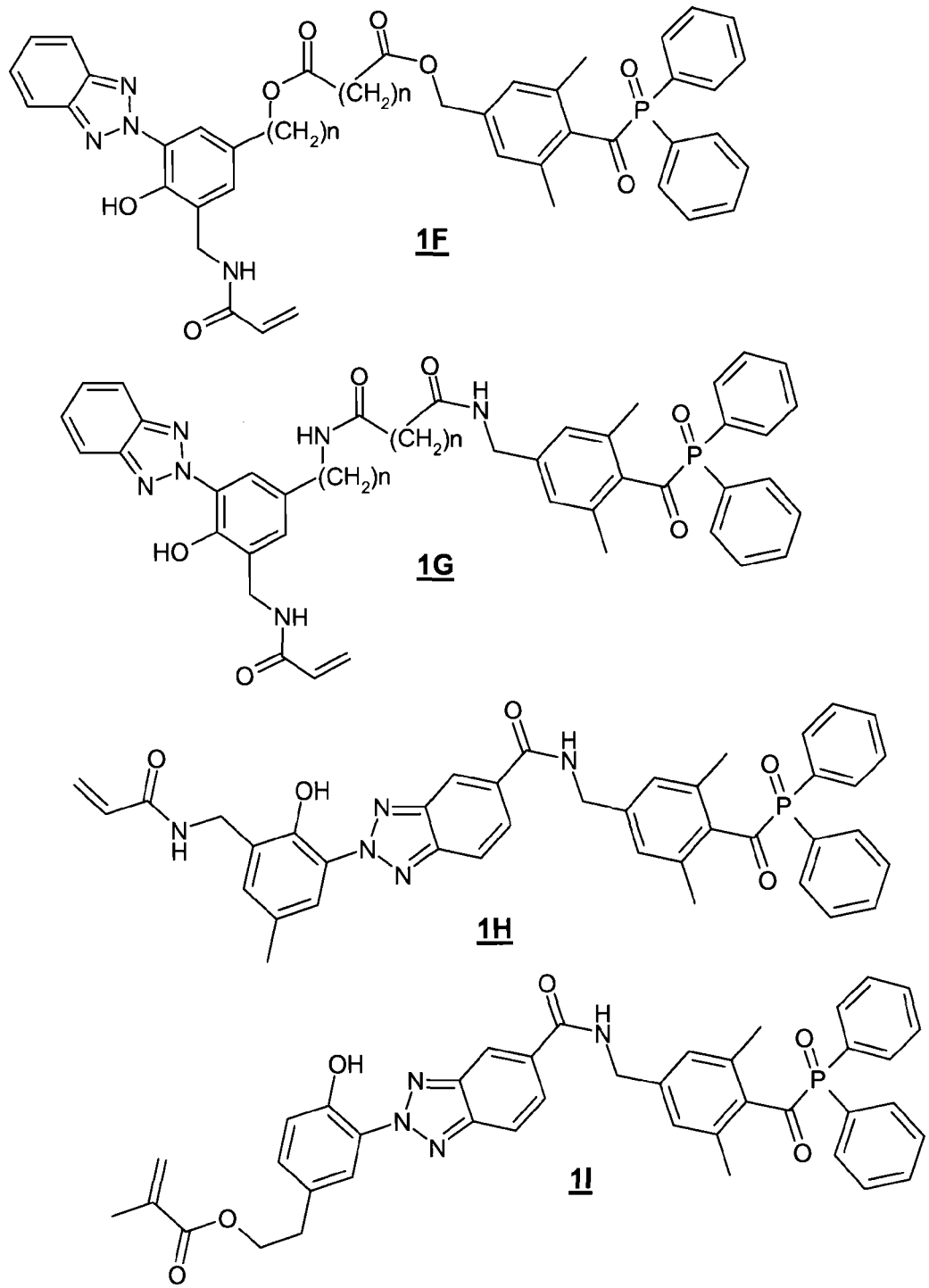
Figure 1:
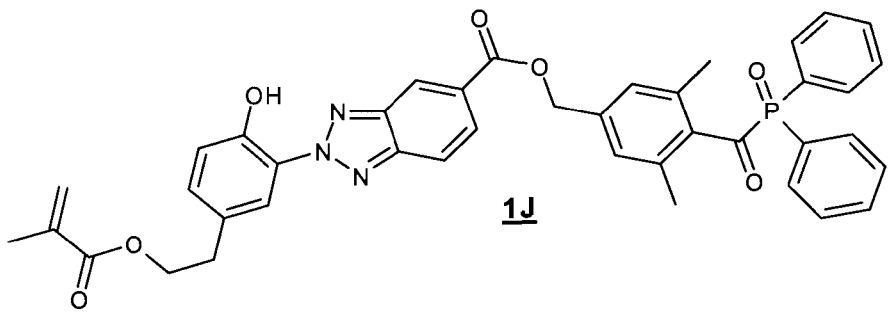
Figure 1:
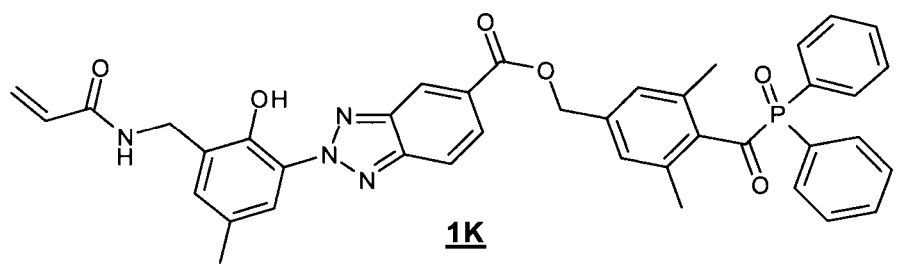
Figure 1:
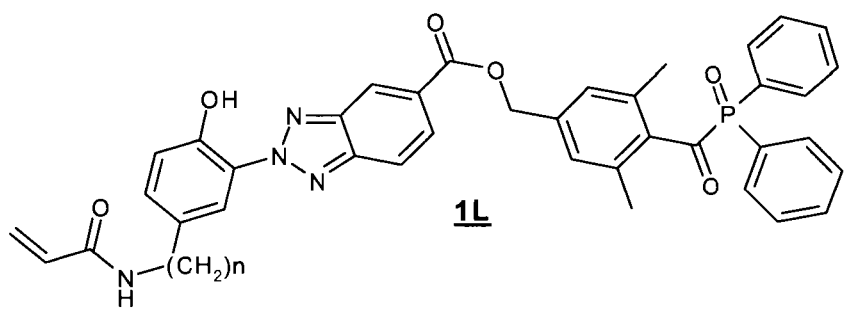
Figure 1:
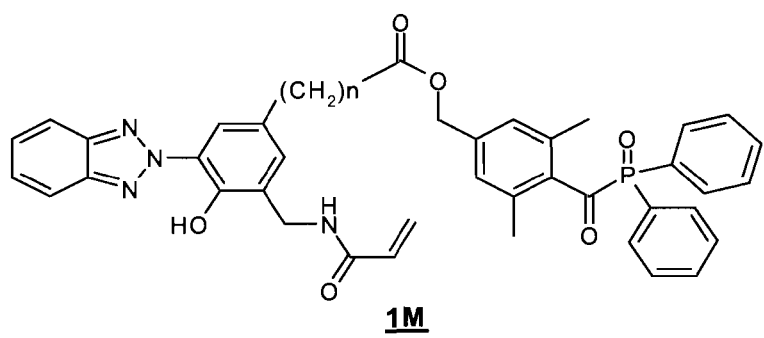
Figure 1:
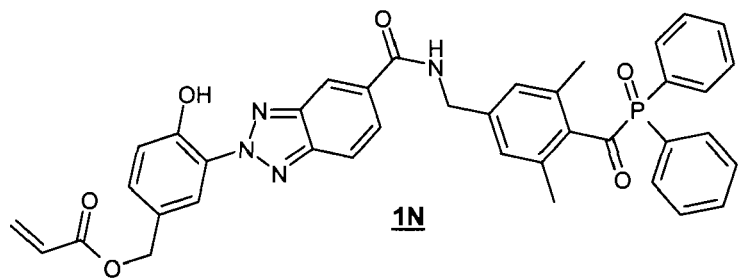
Figure 1:
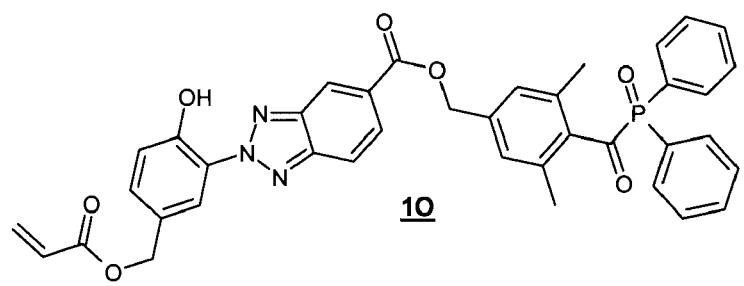
Figure 1:
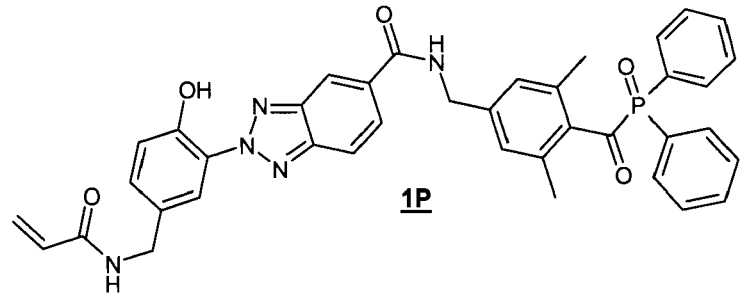
Figure 1:
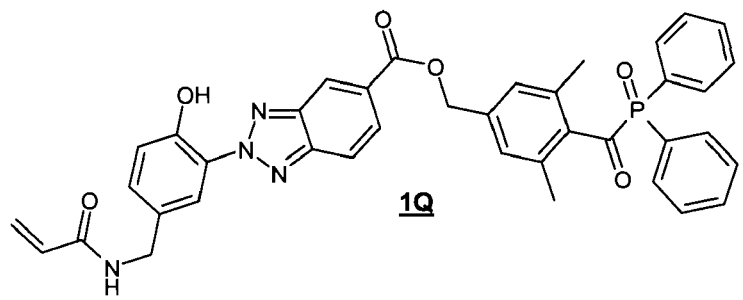
Figure 1:
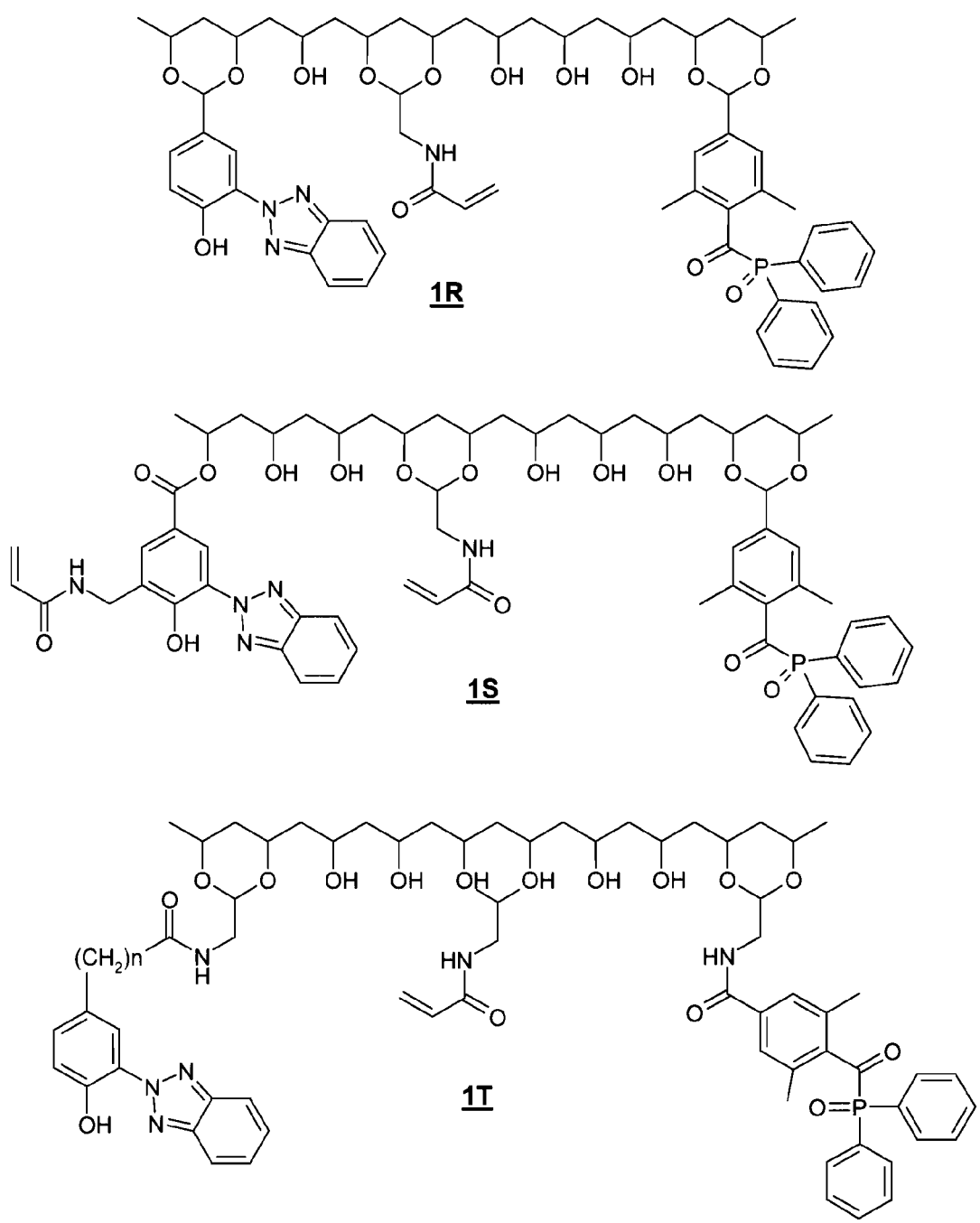
Figure 1:
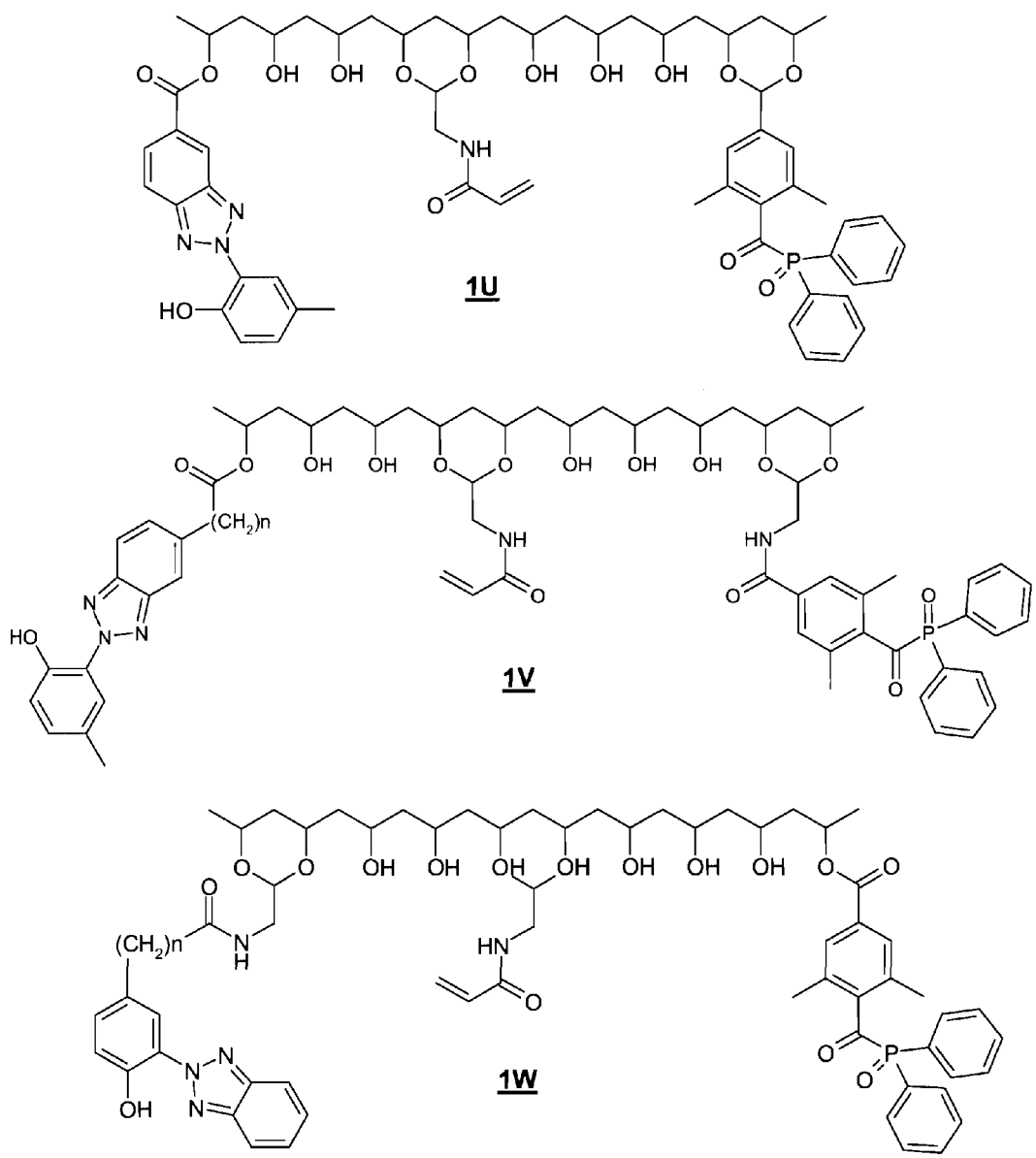
Figure 1:
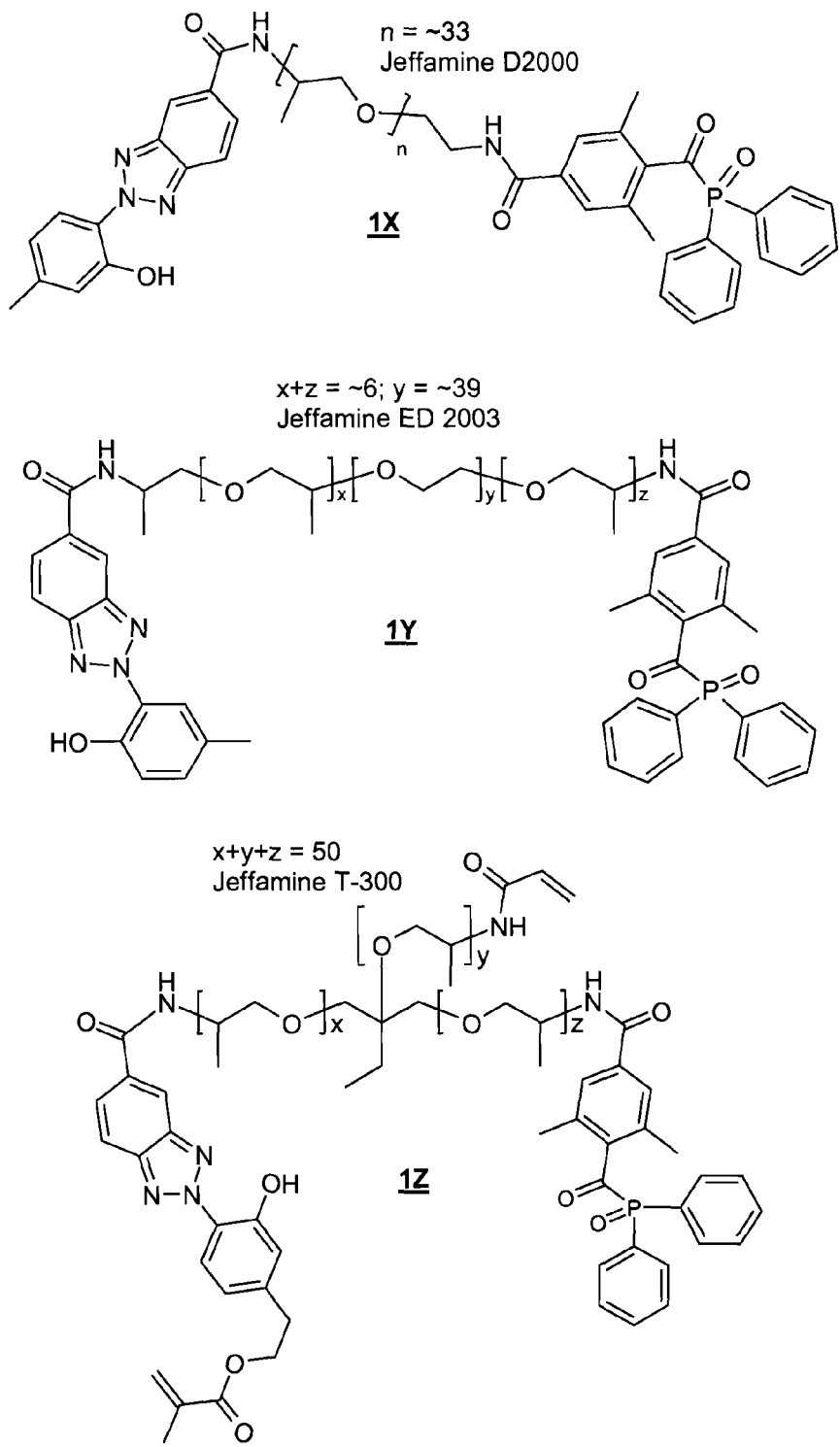

Before the present tri-functional compounds, compositions, and methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a monomer" includes mixtures of two or more such monomers, and the like.

"Optional" or "optionally" means that the subsequently described event or circumstance can or cannot occur, and that the description includes instances where the event or circumstance occurs and instances where it does not. For example, the phrase "optional linker" means that the linker can or cannot be present.

Unless defined otherwise, all technical and scientific terms used herein have the same meaning as commonly understood by one of ordinary skill in the art to which this invention belongs. As employed throughout the disclosure, the following terms, unless otherwise indicated, shall be understood to have the following meanings.

The term "alkyl group" as used herein is a monovalent radical of a branched or unbranched saturated hydrocarbon having 1 to 24 carbon atoms. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "alkoxy group" as used herein has the formula —OR, where R is an alkyl group as defined herein.

The term "aryloxy group" as used herein has the formula —OR', where R' is an aryl group as defined herein.

The term "aralkyl group" as used herein has the formula —R—R', where R and R' are an alkyl group and aryl group, respectively, as defined herein. An example of an aralkyl group is a benzyl group (—CH$_2$Ph).

The term "alkylene" as used herein refers to a divalent radical of hydrocarbon

The term "alkylene oxide group" as used herein is a group composed of one or more repeat units having the formula —(R$^a$)$_n$O—, where R$^a$ is a linear or branched C$_1$-C$_{12}$-alkylene and n is from 1 to 10.

The term "amino group" as used herein has the formula —NR$^b$R$^c$, where R$^b$ and R$^c$ are, independently, hydrogen, a C$_1$-C$_{12}$ linear or branched alkyl group, or a C$_6$-C$_{24}$ aryl group.

The term "alkylene amine group" as used herein is a group composed of one or more repeat units having the formula —(R$^a$)$_n$NR$^d$—, where R$^a$ is a linear or branched C$_1$-C$_4$-alkylene, n is from 1 to 10, and R$^d$ is hydrogen, an alkyl group, or an aryl group.

The term "dicarbonyl group" as used herein is a group or molecule composed of two C=O groups. Each carbonyl group, independently, can be present as an aldehyde, ketone, ester, anhydride, or carboxylic acid group.

The term "silicon group" as used herein is a group or molecule composed of at least one silicon atom. The silicon group can be substituted with one or more alkyl groups, where the alkyl groups can be the same or different.

A "hydrogel" refers to a polymeric material that can absorb at least 10 percent by weight of water when it is fully hydrated. A hydrogel material can be obtained by polymerization or copolymerization of at least one hydrophilic monomer in the presence of or in the absence of additional monomers and/or macromers or by crosslinking of a prepolymer.

A "silicone hydrogel" refers to a hydrogel obtained by copolymerization of a polymerizable composition comprising at least one silicone-containing vinylic monomer or at least one silicone-containing macromer or a silicone-containing prepolymer.

"Hydrophilic," as used herein, describes a material or portion thereof that will more readily associate with water than with lipids.

A "monomer" means a low molecular weight compound that can be polymerized actinically, thermally, or chemically. Low molecular weight typically means average molecular weights less than 700 Daltons.

As used herein, "actinically" in reference to curing or polymerizing of a lens-forming material means that the curing (e.g., crosslinked and/or polymerized) is performed by actinic irradiation, such as, for example, UV irradiation, visible light irradiation, ionized radiation (e.g. gamma ray or X-ray irradiation), microwave irradiation, and the like. Actinic curing methods are well-known to a person skilled in the art.

A "vinylic monomer," as used herein, refers to a low molecular weight compound that has an ethylenically unsaturated group and can be polymerized actinically or thermally. Low molecular weight typically means average molecular weights less than 700 Daltons.

A "hydrophilic vinylic monomer," as used herein, refers to a vinylic monomer that is capable of forming a homopolymer that can absorb at least 10 percent by weight water when fully hydrated. Examples of hydrophilic vinylic monomers include without limitation hydroxyl-substituted lower alkyl (C$_1$ to C$_3$)(meth)acrylates, hydroxyl-substituted lower alkyl vinyl ethers, C$_1$ to C$_3$ alkyl(meth)acrylamide, di-(C$_1$-C$_3$ alkyl)(meth)acrylamide, N-vinylpyrrole, N-vinyl-2-pyrrolidone, 2-vinyloxazoline, 2-vinyl-4,4'-dialkyloxazolin-5-one, 2- and 4-vinylpyridine, amino(lower alkyl)- (where the term "amino" also includes quaternary ammonium), mono(lower alkylamino)(lower alkyl) and di(lower alkylamino)(lower alkyl)(meth)acrylates, allyl alcohol, N-vinyl C$_1$ to C$_3$ alkylamide, N-vinyl-N—C$_1$ to C$_3$ alkylamide, C$_1$-C$_4$-alkoxy polyethylene glycol(meth)acrylate having a weight average molecular weight of up to 1500, and the like. Examples of preferred hydrophilic vinylic monomers are N,N-dimethylacrylamide (DMA), N,N-dimethylmethacrylamide (DMMA), 2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethylmethacrylate (HEMA), 2-hydroxyethyl acrylate (HEA), hydroxypropyl acrylate, hydroxypropyl methacrylate (HPMA), trimethylammonium 2-hydroxy propylmethacrylate hydrochloride, aminopropyl methacrylate hydrochloride, dimethylaminoethyl methacrylate (DMAEMA), glycerol methacrylate (GMA), N-vinyl-2-pyrrolidone (NVP), allyl alcohol, vinylpyridine, a C$_1$-C$_4$-alkoxy polyethylene glycol(meth)acrylate having a weight average molecular weight of up to 1500, N-vinyl formamide, N-vinyl acetamide, N-vinyl isopropylamide, N-vinyl-N-methyl acetamide, allyl alcohol, N-vinyl caprolactam, and mixtures thereof.

A "hydrophobic vinylic monomer," as used herein, refers to a vinylic monomer that is capable of forming a homopolymer that can absorb less than 10 percent by weight water. Nearly any hydrophobic vinylic monomer can be used. Examples of preferred hydrophobic vinylic monomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate, combinations thereof.

A "macromer" refers to a medium to high molecular weight compound or polymer that contains functional groups capable of undergoing further polymerizing/crosslinking reactions. Medium and high molecular weight typically means average molecular weights greater than 700 Daltons. In one aspect, the macromer contains ethylenically unsaturated groups and can be polymerized actinically or thermally.

A "prepolymer" refers to a starting polymer that can be cured (e.g., crosslinked and/or polymerized) actinically or thermally to obtain a crosslinked and/or polymerized polymer having a molecular weight much higher than the starting polymer.

Described herein are tri-functional compounds useful in the production of UV-absorbing ophthalmic lenses. The compounds generally have (1) an ultraviolet absorber moiety (or component), (2) a polymerization initiator moiety, and (3) an olefinically unsaturated group capable of undergoing polymerization. Each component is covalently attached within a single molecule. In one aspect, the tri-functional compound is defined by formula I

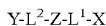

wherein:

Z is a divalent radical which comprises a benzotriazole moiety or benzophenone moiety and is defined by formula (1a), (1b), (1c) or (1d)

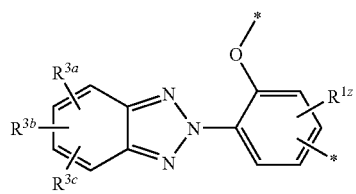

(1a)

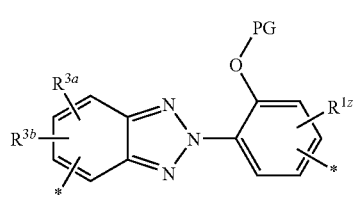

(1b)

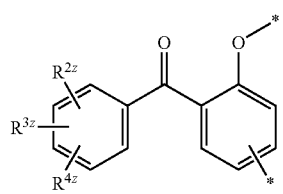

(1c)

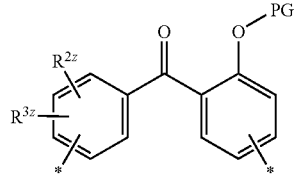

(1d)

in which $R^{3a}$, $R^{3b}$, $R^{3c}$, $R^{2z}$, $R^{3z}$, $R^{4z}$, and $R^{1z}$, independent of another, are hydrogen, halogen (Cl, Br, or I), $C_1$-$C_{12}$ linear or branched alkyl group, $C_1$-$C_{12}$ linear or branched alkoxy group, $C_6$-$C_{24}$ aryl or substituted aryl group, PG is a protective labile group (e.g., $C_1$-$C_{18}$ alkylcarbonyl, tri($C_1$-$C_{12}$ alkyl) silyl, $C_1$-$C_{18}$ linear or branched alkyl, $C_1$-$C_{18}$ linear or branched alkoxyalkyl, and others described later in this application);

X is a monovalent radical comprising a radical initiator moiety selected from the group consisting of phosphine oxide (a trivalent radical

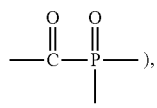

a peroxide group, an azide group, an α-hydroxyketone, or an α-aminoketone;

Y is a monovalent radical of formula (2)

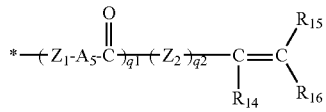

(2)

in which $Z_1$ and $Z_2$ independent of each other are a covalent bond, a linear or branched $C_1$-$C_{12}$ alkylene divalent radical, a linear or branched $C_1$-$C_{12}$ alkylene divalent radical having one or more hydroxyl groups, a radical of —$(CH_2CH_2O)_d$—$CH_2CH_2$— in which d is an integer of 1 to 10, unsubstituted phenylene divalent radical, $C_1$-$C_4$ alkyl or $C_1$-$C_4$ alkoxy substituted phenylene divalent radical, $C_7$-$C_{12}$ aralkylene divalent radical,

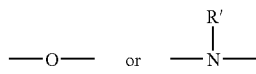

in which R' is H or $C_1$-$C_8$ alkyl; $A_5$ is a covalent bond,

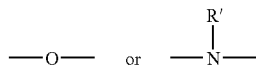

in which R' is H or $C_1$-$C_8$ alkyl; $q_1$ and $q_2$ independent of each other are an integer of 0 or 1; $R_{14}$ is hydrogen, $C_1$-$C_4$ alkyl or halogen; $R_{15}$ and $R_{16}$ independent of each other are hydrogen, $C_1$-$C_4$ alkyl, phenyl, carboxy, halogen, or a radical of

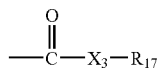

in which $X_3$ is

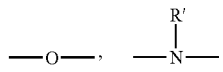

as defined above or —S— and $R_{17}$ is a $C_1$-$C_{12}$ alkyl, $C_1$-$C_{12}$ hydroxyalkyl, $C_1$-$C_{12}$ aminoalkyl, alkylaminoalkyl having up to 24 carbon atoms, or dialkylaminoalkyl having up to 24 carbon atoms; and $L^1$ and $L^2$ independently of each other are a covalent bond or a linker.

Each component is described in detail below.

In a preferred embodiment, the ultraviolet absorber comprises a benzotriazole or a benzophenone. Many benzotriazole and benzophenone UV absorbers are known and many are commercially available. The identity of the benzotriazole or benzophenone UV absorber is not critical, but should be selected based on its characteristic UV cut-off to give the desired UV absorbing property. In one aspect, the benzotriazole UV absorber can be a hydroxyphenyl-benzotriazole and the benzophenone UV absorber can be a hydroxyphenylbenzophenone. Preferably, the UV absorber moiety Z of the tri-functional compound has the formula (1a) in which $R^{3b}$, $R^{3c}$ and $R^{1z}$ are hydrogen and $R^{3a}$ is $R^3$ which is hydrogen, halogen, a $C_1$-$C_{12}$ linear or branched alkyl group, a $C_1$-$C_{12}$ linear or branched alkoxy group, or a $C_6$-$C_{24}$ aryl or substituted aryl group, as shown by formula X

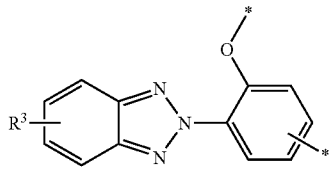

X

The tri-functional compounds described herein contain one or more polymerization initiator moieties directly or indirectly bonded to the ultraviolet absorber component. The initiator can be a thermal initiator (i.e., initiates polymerization by exposure to heat) or photoinitiator (e.g., when exposed to actinic energy). Preferably, when the initiator is a photoinitiator, the photoinitiator moiety comprises a phosphine oxide, a peroxide group, an azide group, an α-hydroxyketone, or an α-aminoketone. Other type 1 and type 2 initiators can be also used such as, for example, thioxanthones and benzildimethylketals.

Examples of preferred phosphine oxide photoinitiator moieties comprise a monovalent radical of formula XI

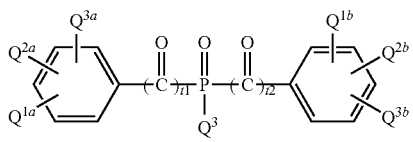

XI wherein t1 and t2 independent of each other are 0 or 1 provided that at least one of t1 and t2 is 1, one of $Q^{1a}$ and $Q^{1b}$ is a covalent bond (connecting to a linker or directly to the UV-absorber moiety) and the other is hydrogen. $C_1$-$C_{12}$ linear or branched alkyl group, or $C_1$-$C_{12}$ linear or branched alkoxy group, $Q^{2a}$, $Q^{2b}$, $Q^{3a}$, $Q^{3b}$ independently of one another hydrogen are $C_1$-$C_{12}$ linear or branched alkyl group, or $C_1$-$C_{12}$ linear or branched alkoxy group.

Examples of preferred peroxide groups as initiator moieties are those of formula XII

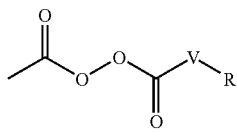

XII where V is a covalent bond or oxygen and R is a $C_1$-$C_{20}$ linear or branched alkyl group (e.g., for example, —$(CH_2)_n$H (n=1-18); —$CH(CH_3)CH_3$; —$C(CH_3)_3$; —$CH(CH_3)CH_2CH_3$; —$C(CH_3)_2CH_2C(CH_3)_3$; —$C(CH_3)_2(CH_2)_4H$; —$C(CH_2CH_3)_2(CH_2)_4H$; —$C(CH_3)_2(CH_2)_5H$; —$C(CH_2CH_3)_2(CH_2)_5H$; —$C(CH_3)_2(CH_2)_6H$; or —$C(CH_2CH_3)_2(CH_2)_6H$) or phenyl group.

Examples of azide groups (—N=N—) are provided in International Patent Application Publication No. WO 2004/062371. For example, 4,4'-azobis(4-cyanopentanoic acid) manufactured by Wako Chemicals can be used herein.

In another preferred embodiment, the monovalent photoinitiator moiety comprises a monovalent radical of an α-hydroxyketone or an α-aminoketone of the formula IIa or IIb

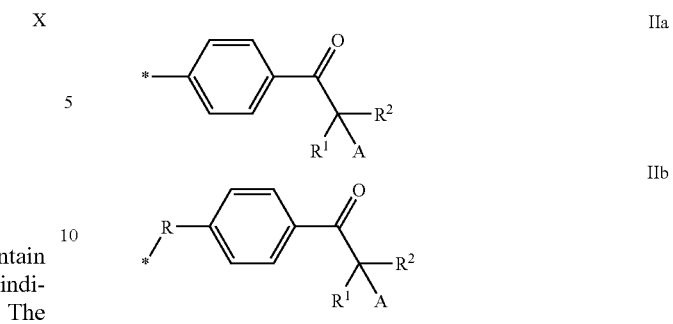

IIa

IIb wherein R is oxygen, nitrogen, a linear or branched $C_1$-$C_{12}$ alkylene divalent radical, a divalent radical of —$OCH_2CH_2O$—, a divalent radical of

in which $R''$ is hydrogel or a $C_1$-$C_{12}$ alkyl radical and alk is $C_1$-$C_{12}$ alkylene divalent radical, or combinations thereof, $R^1$ and $R^2$ are, independently, hydrogen, a $C_1$-$C_{12}$ linear or branched alkyl group, a $C_6$-$C_{24}$ aryl or substituted aryl group, a $C_7$-$C_{24}$ aralkyl group; and A comprises a hydroxyl group, a $C_1$-$C_{12}$ alkoxy group, a $C_6$-$C_{24}$ aryloxy group, or a primary, secondary or tertiary amino group.

Preferably, the monovalent photoinitiator moiety comprises the formula III or Iva or b

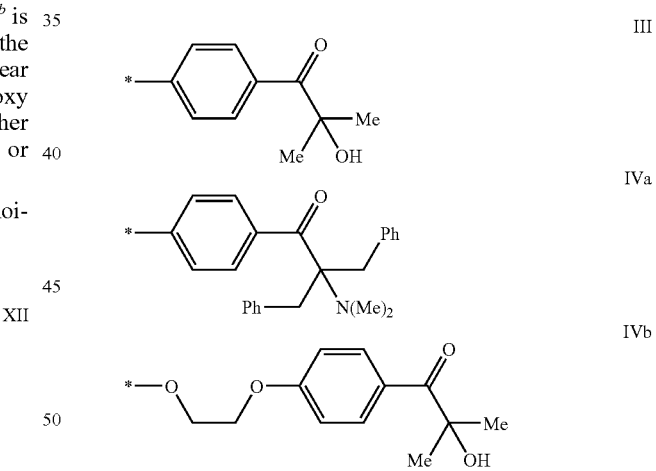

III

IVa

IVb in which Ph is phenyl and Me is methyl.

Functionalized α-hydroxyketones suitable for use as UV polymerization initiators are commercially available. For example, 2-hydroxy-1-[4-(2-hydroxy-ethoxy)phenyl]-2-methylpropan-1-one (Irgacure® 2959, Ciba Specialty Chemicals) contains a free primary hydroxyl group that can be used to directly or indirectly bond the photoinitiator to the ultraviolet absorber component. Other examples of commercially available α-hydroxyketones include, but are not limited to, Irgacure® 369 and 379 and Darocure 1173.

The tri-functional compounds described herein also include one or more olefinic groups. The term "olefinic group" or "ethylenically unsaturated group" is defined in this application as any group containing at least one C=C group.

Exemplary olefinic groups include without limitation acrylate, methacrylate, acrylamide, methacrylamide, allyl, vinyl, vinylester, or styrenyl. The olefinic groups are capable of being polymerized with other monomers or polymers having olefinic groups upon exposure with actinic radiation or heating.

In another preferred embodiment, when the initiator and/or olefinic group are indirectly bonded to the ultraviolet absorber, a linker can be used. A variety of different groups can be used as the linker. The length of the linker can vary as well. Additionally, the selection of the linker can vary the hydrophilic/hydrophobic properties of the tri-functional compound. This is particularly useful when certain solvents are used during the manufacturing of the ophthalmic lens. Examples of linkers ($L^1$ and/or $L^2$) useful herein include, but are not limited to, a silicon group, a carbonyl group, a dicarbonyl group, a $C_1$ to $C_{12}$ linear or branched alkylene group, a $C_1$ to $C_{12}$ linear or branched alkylene oxide group, a $C_6$ to $C_{24}$ arylalkylene or arylene divalent radical (e.g., -Ph- or —CH (Ph)-), $C_1$ to $C_{12}$ linear or branched alkylene amine group,

or combinations thereof. Any combination of these groups is also contemplated.

Preferably, $L^1$ and $L^2$ in formula I independently of each other are a covalent bond or a divalent radical of —$X_a$-$E_1$-$X_b$-$E_2$-$X_c$—
in which:
$X_a$ is a covalent bond, carbonyl

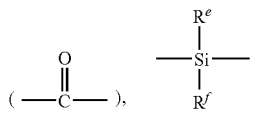

in which $R^e$ and $R^f$ independently of each other are a $C_1$-$C_8$-alkyl, phenyl or a $C_1$-$C_4$ alkyl- or $C_1$-$C_4$-alkoxy-substituted phenyl, a divalent radical of —$(R^aO)_n$— in which $R^a$ is a linear or branched $C_1$-$C_{12}$-alkylene and n is from 1 to 10,

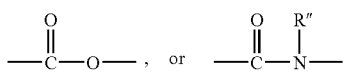

in which R" is H or $C_1$-$C_8$ alkyl;
$E_1$ and $E_2$ independently of each other are a covalent bond, a divalent radical of —$(R^aO)_n$— in which $R^a$ and n are defined above,

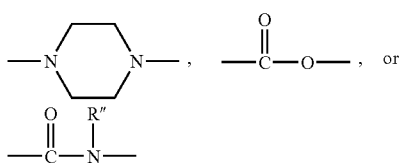

in which R" is H or $C_1$-$C_8$ alkyl, a $C_1$ to $C_{12}$ linear or branched alkylene divalent radical, a cycloalkyl diradical with up to 40 carbon atoms, an alkylcycloalkyl diradical with up to 40 carbon atoms, an alkylaryl diradical with up to 40 carbon atoms, an arylalkylene divalent radical with up to 40 carbon atoms, or a dicarbonyl group having the formula J—C(O)$L^3$C(O)— in which $L^3$ is a $C_1$ to $C_{12}$ linear or branched alkylene divalent radical or —$(R^{e1}$—O$)_{w1}$—$(R^{e2}$—O$)_{w2}$—$(R^{e3}$—O$)_{w3}$—, wherein $R^{e1}$, $R^{e2}$, and $R^{e3}$ independently of one another are a linear or branched $C_1$-$C_4$-alkylene and w1, w2 and w3 independently of one another are a number from 0 to 20 provided that the sum of (n+m+p) is 1 to 60; and $X_b$ and $X_c$ independently of each other are a covalent bond,

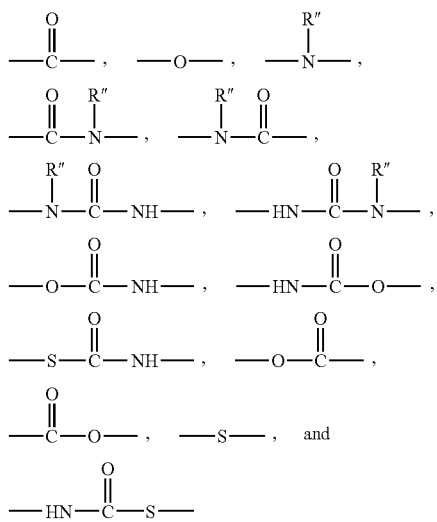

in which R" is defined above. Other specific examples of linkers useful herein are described below.

FIG. 1 also provides specific examples of preferred tri-functional compounds described herein that have specific linkers present in the compounds.

In one aspect, the tri-functional compound comprises the formula V

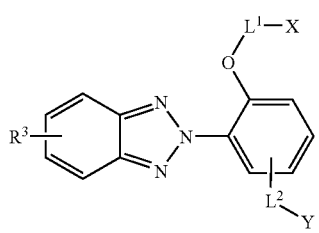

wherein: $R^3$ is hydrogen, a $C_1$-$C_{12}$ linear or branched alkyl group, a halogen, a $C_6$ to $C_{24}$ aryl group, a $C_7$ to $C_{24}$ aralkyl, or a $C_1$ to $C_{12}$ linear or branched alkoxy group; $L^1$ and $L^2$ are, independently, a linker as described above; X comprises a polymerization initiator as described above; and Y comprises an olefinic group as described above.

In one aspect, $R^3$ in formula V is hydrogen. In another aspect, X in formula V comprises a monovalent radical of the formula VI

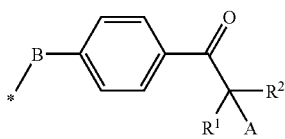

VI wherein: $R^1$ and $R^2$ are, independently, hydrogen, a $C_1$-$C_{12}$ linear or branched alkyl group, a $C_6$-$C_{24}$ aryl or substituted aryl group, a $C_7$-$C_{24}$ aralkyl group; and A is a hydroxyl group, a $C_1$-$C_{12}$ alkoxy group, a $C_6$-$C_{24}$ aryloxy group, or an amino group; and B is a silicon group, a carbonyl group, a dicarbonyl group, a $C_1$-$C_{12}$ linear or branched alkylene group, a $C_1$-$C_{12}$ linear or branched alkylene oxide group, a $C_1$-$C_{12}$ linear or branched alkylene amine group, or any combination thereof. In a further aspect, -$L^2$-Y in formula V comprises the formula —$(CH_2)_tUC(O)C(R^4)$=$CH_2$, wherein t is from 1 to 3, U is O or NH, and $R^4$ is hydrogen or methyl.

Another preferred tri-functional compound has the formula VII

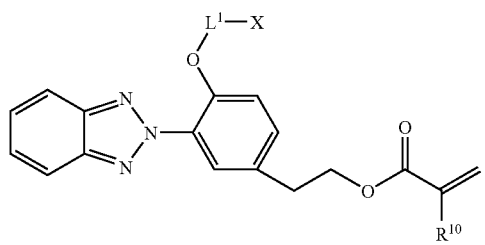

VII wherein $R^{10}$ is hydrogen or methyl, $L^1$ and X are those described above. Preferably, $L^1$ can be derived from any protective labile group described herein including, for example, those provided in Table 1 below, which can be combined with alkyl, aralkyl, aryl, alkoxy, aryloxy, or aralkyloxy groups. A preferred $L^1$ can have the formula

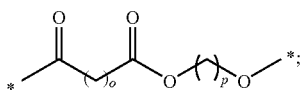

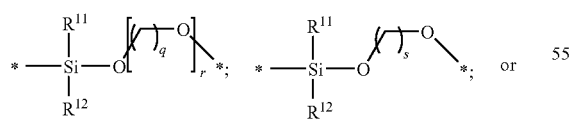

wherein: o, p, q, r, s, u, and v are, independently, an integer from 1 to 5; $R^{11}$ and $R^{12}$ are, independently, hydrogen or a $C_1$-$C_{12}$ linear or branched alkyl group. X preferably comprises the formula

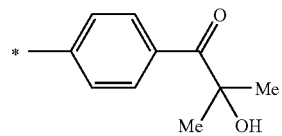

In one aspect, the tri-functional compound comprises the formula VIII

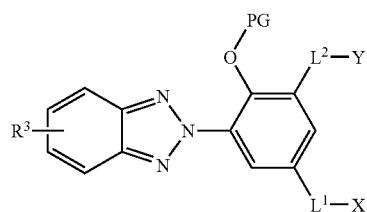

VIII wherein: $R^3$ is hydrogen, a $C_1$-$C_{12}$ linear or branched alkyl group, a halogen, a $C_6$ to $C_{24}$ aryl group, a $C_7$ to $C_{24}$ aralkyl, or a $C_1$ to $C_{12}$ alkoxy group; $L^1$ and $L^2$ independently of each other is a linker described above; X comprises a polymerization initiator described above; Y comprises an olefinic group described above; and PG is a protective labile group.

In another aspect, the tri-functional compound comprises the formula IXa or b

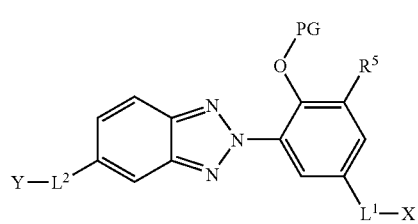

IXa

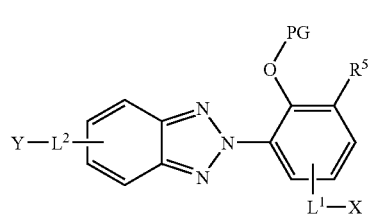

IXb wherein: $R^5$ is hydrogen, a $C_1$-$C_{12}$ linear or branched alkyl group, a $C_1$-$C_{12}$ linear or branched alkoxy group, or a $C_6$-$C_{24}$ aryl or substituted aryl group; $L^1$ and $L^2$ comprise, independently, a linker described above; X comprises a polymerization initiator described above; Y comprises an olefinic group described above; and PG comprises a protective group.

In one aspect, the tri-functional compound comprises the formula X

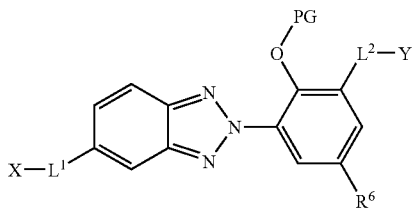

wherein: $R^6$ comprises hydrogen, a $C_1$-$C_{12}$ linear or branched alkyl group, a $C_1$-$C_{12}$ linear or branched alkoxy group, or a $C_6$-$C_{24}$ aryl or substituted aryl group; $L^1$ and $L^2$ comprise, independently, a linker described above; X comprises a polymerization initiator described above; Y comprises an olefinic group described above; and PG comprises a protective group described above.

Depending upon the structure of the tri-functional compounds, the compounds can be designed so that the UV absorber component essentially absorbs no energy at a particular wavelength. As will be discussed in greater detail below, by minimizing the amount of energy absorbed by the UV absorber component, shorter curing times can be achieved. This is due in part to the efficient activation of the initiator by the energy source without any interference (i.e., competition) by the UV absorber component. Additionally, homogeneous curing can be achieved using the tri-functional compounds, which is another desirable feature in the manufacturing of ophthalmic lenses.

In certain aspects, the UV absorber component of the tri-functional compound can have one or more protecting groups that essentially prevent the absorption of energy by the UV absorber component. Thus, in this aspect, the protective group can render the UV absorber component essentially non-UV-absorbing. In general, the protective group is any group that can be readily cleaved using techniques known in the art. Examples of protecting groups include, but are not limited to, a silyl group or ester group. In one aspect, when a silyl group or carbonyl group is bonded to an aromatic oxygen, the silyl group or carbonyl group can be cleaved by varying the pH. A list of protecting groups and deprotection methods useful herein is provided in Table 1.

TABLE 1

| Protecting Group | Deprotection methods |
| --- | --- |
| Methyl Ether | pH < 1 and 100° C.; $RS^+$, $N_3^+$, $SCN^+$ and NaCN pH 12 nucleophilic reagents; $AlCl_3$ at 80° C. Lewis acids |
| Methoxymethyl Ether | pH 1; Zn/HCl 1 electron reductions; $AlCl_3$, $SnCl_4/BF_3$, and TsOH at 80° C. Lewis acids; HBr/In• free radical reactions; heat >350° C.; C+/olefin electrophilic reagents |
| 2-Methoxyethoxymethyl Ether | pH < 1; $AlCl_3$ at 80° C. and TsOH at 80° C. Lewis acids; heat >350° C. |
| Methylthiomethyl Ether | pH < 1; Zn/HCl and Zn/AcOH 1 electron reductions; $AlCl_3$ Lewis acids; Hg(II) soft acids, HBr/In• free radical reactions; heat >350° C. |
| Phenacyl Ether | pH < 1 and 100° C.; pH > 12 and 150° C.; Zn/HCl, Zn/AcOH, and Cr(II) at pH 5 1 electron reductions; $AlCl_3$ Lewis acids |
| Allyl Ether | pH < 1 and 100° C.; pH > 12 and 150° C.; $AlCl_3$ Lewis acid; $SeO_2$ at pH 2-4 oxidations |
| Cyclohexyl Ether | pH < 1 |
| t-Butyl Ether | pH 1; Zn/HCl 1 electron reductions; $AlCl_3$, $SnCl_4/BF_3$, and TsOH at 80° C. Lewis acids; heat >350° C.; C+/olefin electrophilic reagents |
| Benzyl Ether | pH 1; $H_2$/Raney (Ni), $H_2$/Pt pH 2-4, $H_2$/Rh and $H_2$/Pd catalytic reductions; $AlCl_3$ at 80° C. Lewis acids |
| o-Nitrobenzyl Ether | pH < 1 and 100° C.; $H_2$/Raney (Ni), $H_2$/Pt pH 2-4, $H_2$/Rh and $H_2$/Pt catalytic reductions; $AlCl_3$ at 80° C. Lewis acids |
| 9-Anthrylmethyl Ether | pH < 1 and 100° C.; $RS^+$, $N_3^+$, $SCN^+$ nucleophilic reagents; $H_2$/Raney (Ni), $H_2$/Pt pH 2-4, $H_2$/Rh and $H_2$/Pd catalytic reductions; $AlCl_3$ at 80° C. Lewis acids |
| 4-Picolyl Ether | pH < 1 and 100° C.; $H_2$/Raney (Ni), $H_2$/Pt pH 2-4, $H_2$/Rh and $H_2$/Pd catalytic reductions; $AlCl_3$ Lewis acids |
| t-Butyldimethylsilyl Ether | pH from 2-4; pH > 12 at 150° C.; $H_2$/Pt pH 2-4 catalytic reductions; Zn/HCl 1 electron reductions; $AlCl_3$ at 80° C. and TsOH at 80° C. Lewis acids; HBr/In• free radical reactions |
| Aryl Acetate | pH 1; pH from 8.5 to 10; $CH_3S(O)CH_2^-Na^+$ and $NaNH_2$ bases; MeONa, enolate, $NH_3/RNH_2$, and NaCN pH 12 nucleophiles; $LiAlH_4$, Li-s-$Bu_3BH$, i-$Bu_2AlH$ hydride reductions; TsOH at 80° C. Lewis acids; $H_2O_2$ at pH 10-12 and NaOCl at pH 10 oxidations; and $K_2CO_3$/MeI |
| Aryl Pivaloate | pH < 1 and 100° C.; pH > 12 at 150° C.; $LiAlH_4$ hydride reductions; heat >350° C.; |

TABLE 1-continued

| Protecting Group | Deprotection methods |
| --- | --- |
| Aryl Benzoate | pH 1; pH > 12; $CH_3S(O)CH_2^-Na^+$ and $NaNH_2$ bases; NaCN pH 12 nucleophiles; $LiAlH_4$ and i-$Bu_2AlH$ hydride reductions; TsOH at 80° C. Lewis acids; $H_2O_2$ at pH 10-12 oxidations |
| Aryl 9-Fluorenecarboxylate | pH < 1 and 100° C.; pH > 12; $NaNH_2$ bases; NaCN pH 12 nucleophiles; $LiAlH_4$, Li-s-$Bu_3BH$, and i-$Bu_2AlH$ hydride reductions; $AlCl_3$ and TsOH at 80° C. Lewis acids |
| Aryl Methyl Carbonate | pH from 2-4; pH > 12; $CH_3S(O)CH2^-Na^+$ and $NaNH_2$ bases; $RS^+$, $N_3^+$, $SCN^+$ and NaCN pH 12 nucleophilic reagents; RLi and RMgX organometallic reagents; $H_2$/Pt pH 2-4 catalytic reductions; Zn/HCl and Zn/AcOH 1 electron reductions; $LiAlH_4$ and i-$Bu_2AlH$ hydride reductions; $AlCl_3$ and TsOH at 80° C. Lewis acids; HBr/In• free radical reactions; $CrO_3$ at pH 1; $SeO2$ at pH 2-4 oxidations; heat >350° C. |
| Aryl 2,2,2-Trichloroethyl Carbonate | pH < 1 and 100° C.; pH from 10-12; $NaNH_2$ bases; NaCN pH 12 nucleophiles; RLi and RMgX organometallic reagents; Zn/HCl, Zn/AcOH, and Cr(II) at pH 5 1 electron reductions; $LiAlH_4$ and i-$Bu_2AlH$ hydride reductions; $AlCl_3$ and TsOH at 80° C. Lewis acids; heat >350° C.; $K_2CO_3$/MeI |
| Aryl Vinyl Carbonate | pH < 1 and 100° C.; pH from 10-12; $CH_3S(O)CH_2^-Na^+$ and $NaNH_2$ bases; and NaCN pH 12 nucleophilic reagents; RLi and RMgX organometallic reagents; Zn/HCl 1 electron reductions; $LiAlH_4$ and i-$Bu_2AlH$ hydride reductions; $AlCl_3$ and TsOH at 80° C. Lewis acids; Hg(II) soft acids; heat >350° C.; $K_2CO_3$/MeI |
| Aryl Benzyl Carbonate | pH < 1; pH > 12; $CH_3S(O)CH_2^-Na^+$ and $NaNH_2$ bases; NaCN pH 12 nucleophilic reagents; RLi and RMgX organometallic reagents; $H_2$/Raney (Ni), $H_2$/Pt pH 2-4, and $H_2$/Pd catalytic reductions; $LiAlH_4$ and i-$Bu_2AlH$ hydride reductions; $AlCl_3$ and TsOH at 80° C. Lewis acids; heat >350° C. |
| Aryl Methansulfonate | pH > 12; $CH_3S(O)CH_2^-Na^+$ bases; RLi organometallic reagents; $AlCl_3$ at 80° C. Lewis acids; |

Methods for deprotecting the compound when a protecting group is present include, for example, dipping the finished ophthalmic device in a highly basic solution. In one aspect, the device can be dipped in an aqueous solution having a pH greater than 10, greater than 11, or greater than 12 followed by drying. In other aspects, deprotection can be accomplished by exposing the device to heat. For example, the device can be placed in an autoclave and heated for a sufficient time and temperature to cleave the protecting group.

In other aspects, the initiator (and optional linker) can act as the protecting group. For example, with the tri-functional compounds having the formula V and VII, $L^1$-X is bonded to the aromatic oxygen of the UV absorber component of the tri-functional compound, which can render the UV absorber component essentially non-UV-absorbing.

Figure 2:
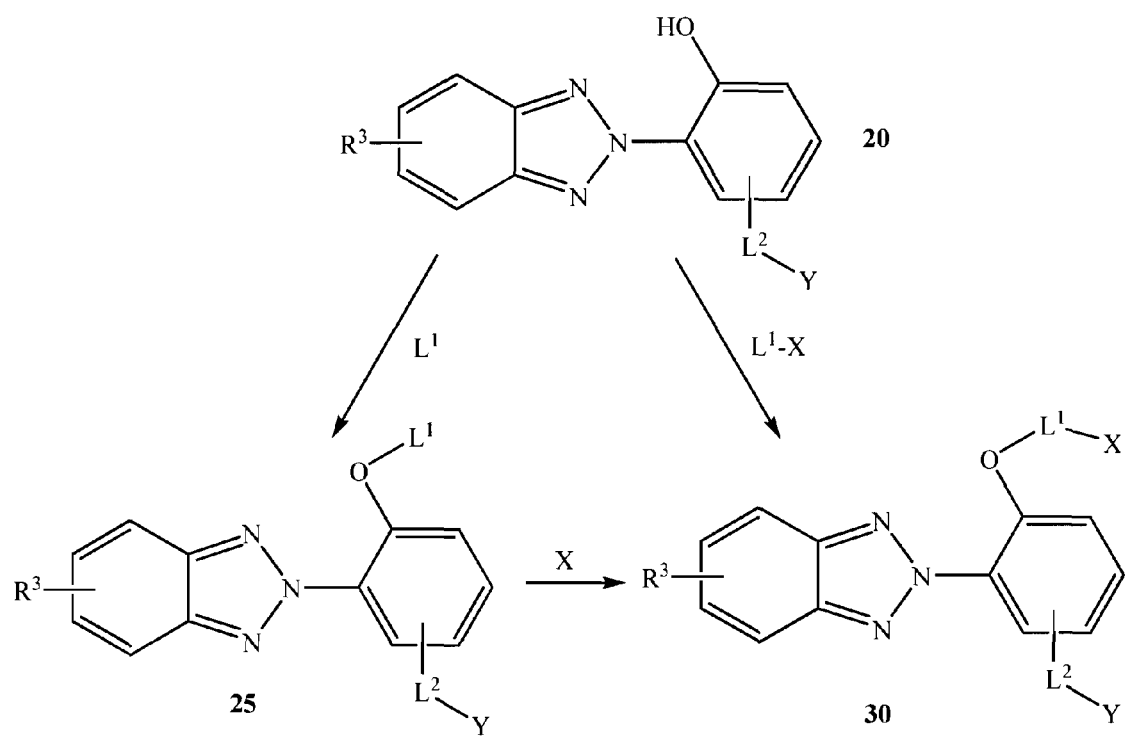
FIGS. 2-8 show exemplary reaction schemes for producing preferred tri-functional compounds of the invention.
Figure 3:
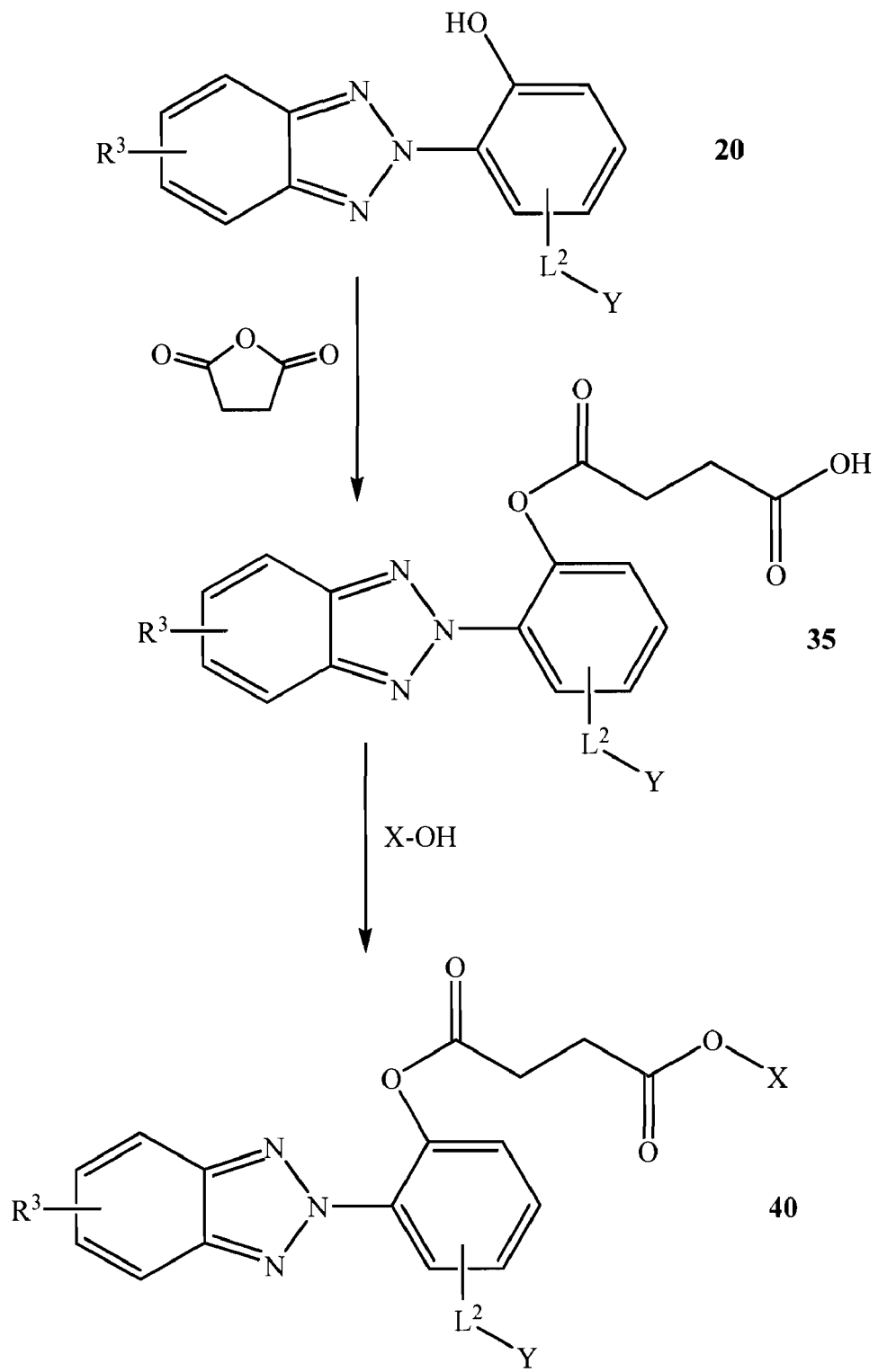
Figure 4:
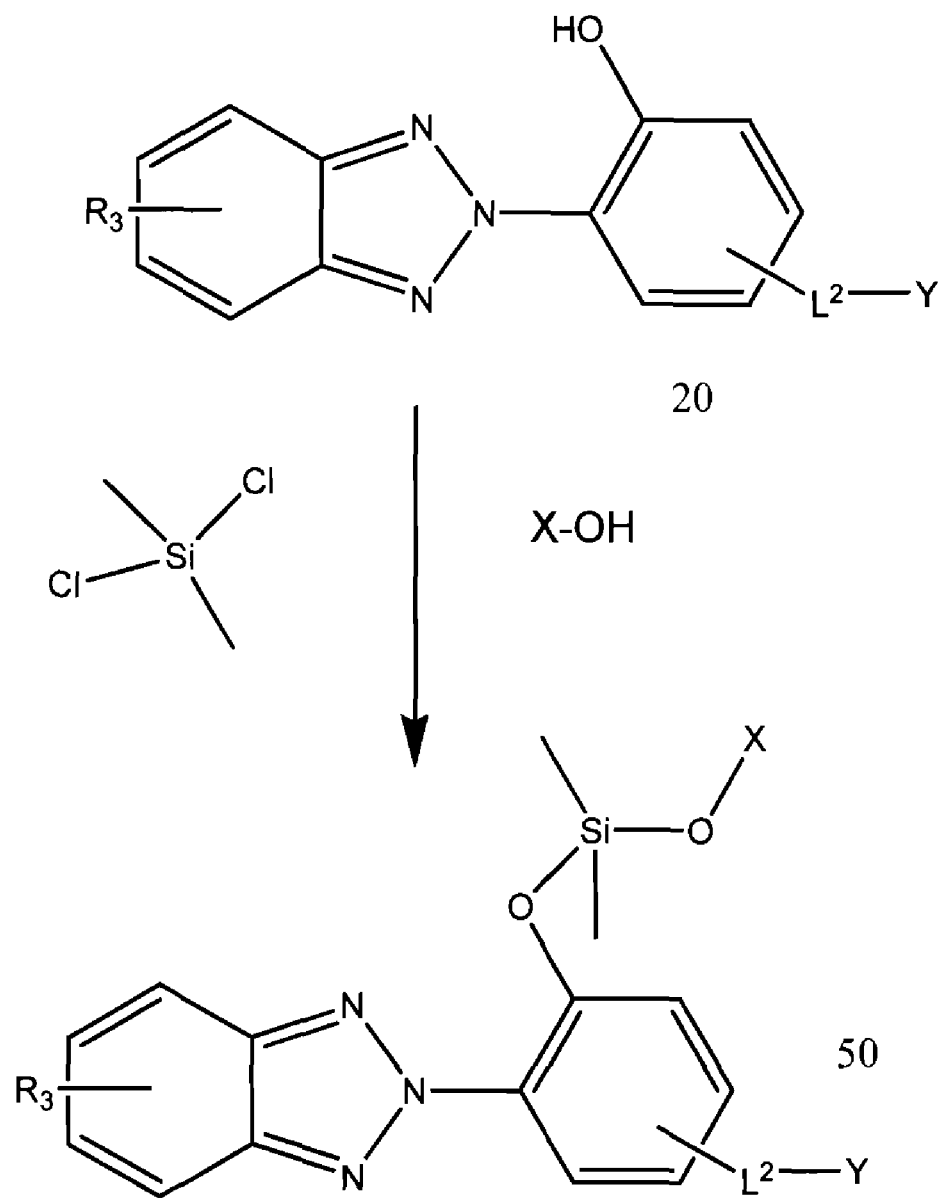
Figure 5:
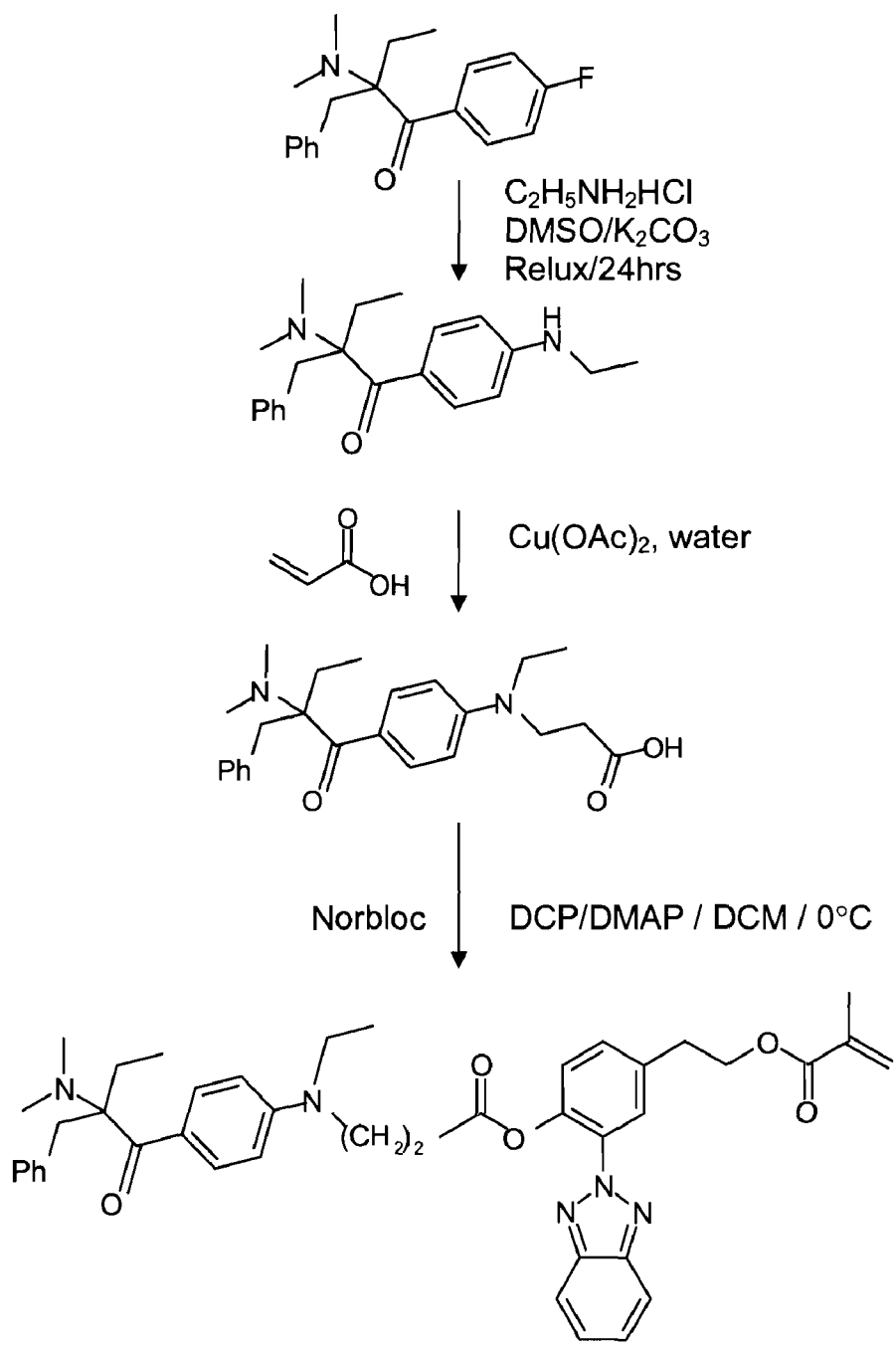
Figure 6:
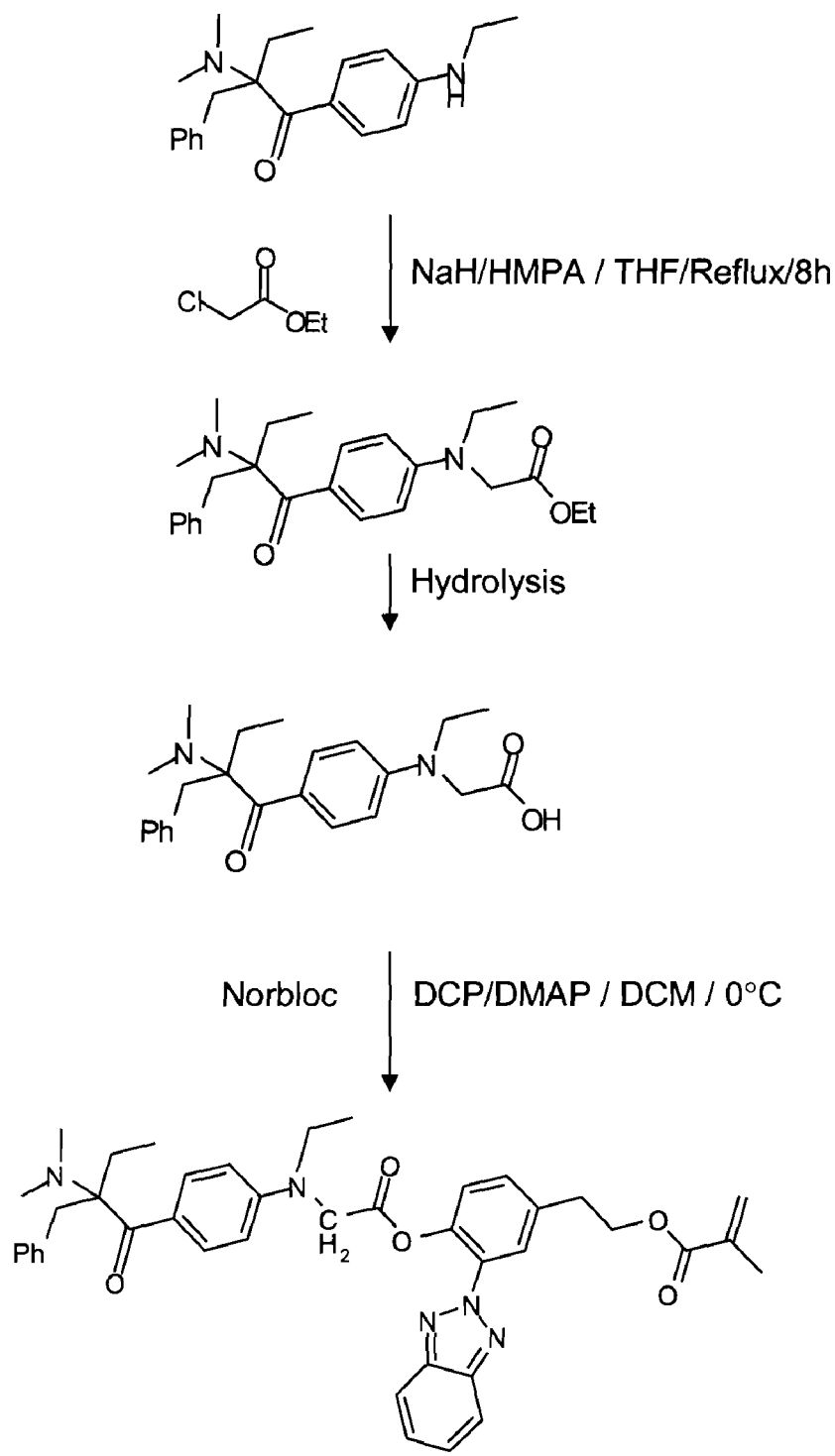
Figure 7:
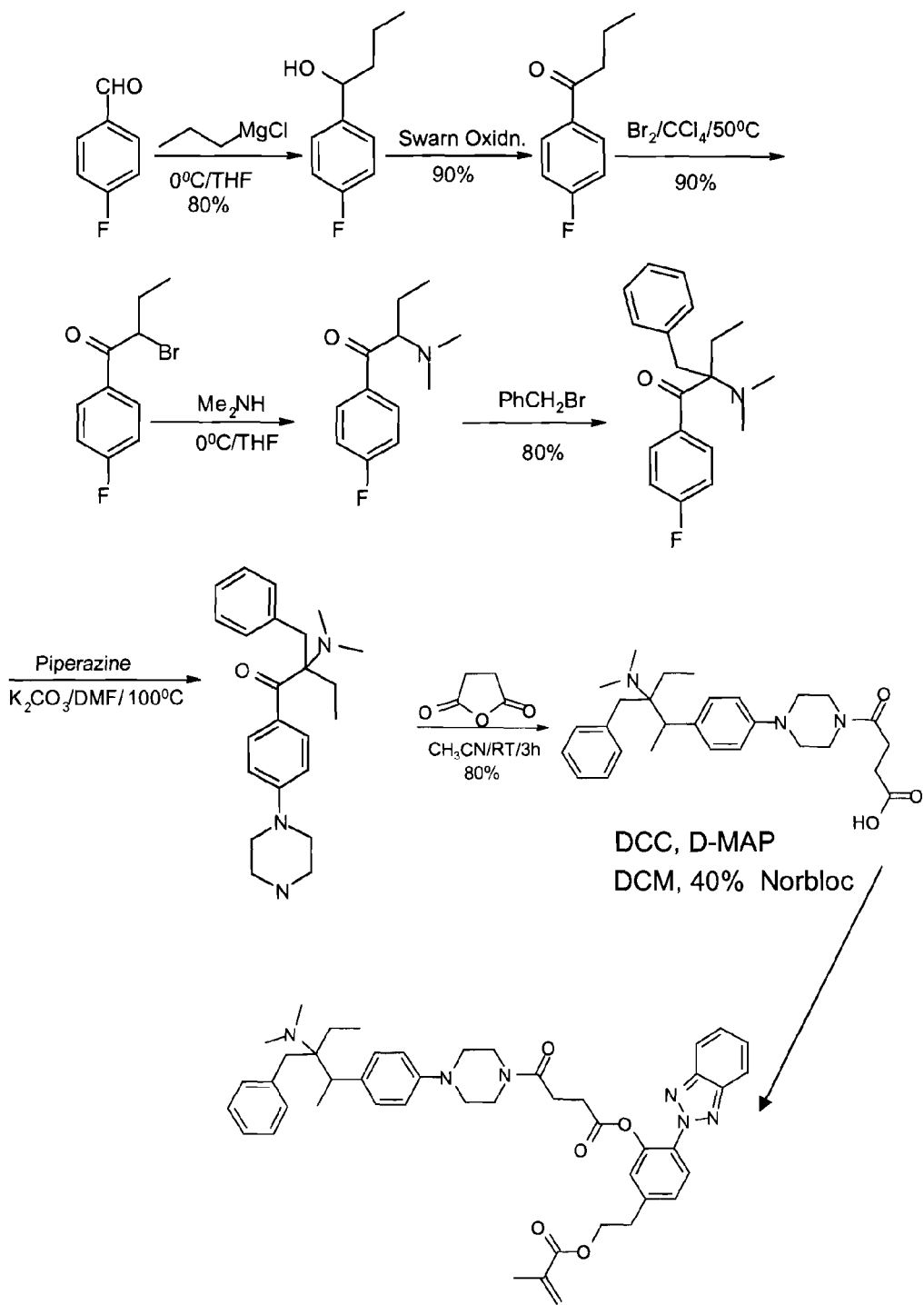
Figure 8:
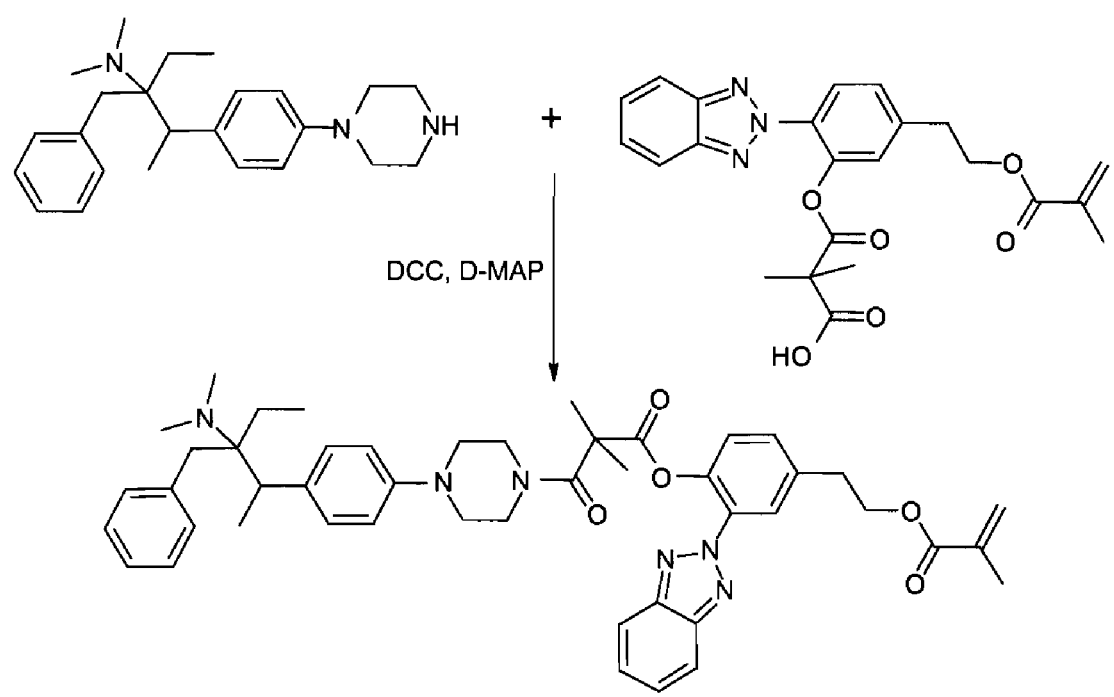

The tri-functional compounds described herein can be synthesized using techniques known in the art. Exemplary reaction sequences for making the tri-functional compounds described herein are provided in FIGS. 2-8. Referring to FIG. 2, the compound 20 can be reacted with a linker $L^1$ to produce compound 25. For example, the linker can be any compound that can react with an aromatic hydroxyl group. The compound having the formula 25 can then be subsequently reacted with initiator X to produce generic compound 30. Alternatively, a compound having the formula 20 can be reacted with a compound having the formula $L^1$-X, where the linker is covalently bonded to the initiator prior to reacting with a compound having the formula 20, and the linker has a functional group that can react with the aromatic hydroxyl group of the UV absorber component. FIG. 3 provides a specific example of a reaction sequence. A compound having the formula 20 is first reacted with succinic anhydride (i.e., the linker) to produce a compound having the formula 35. Next, the compound having the formula 35 is reacted with X—OH, where X is a residue of an initiator. For example, X—OH can be Irgacure® 2959, where the hydroxyl group pendant to the aromatic ring can react with the free carboxylic acid group of 35 to produce a compound having the formula 40. Another synthetic approach is depicted in FIG. 4, where compound 20 is reacted first with a silyl compound (e.g., $SiMe_2Cl_2$) followed by X—OH (e.g., an initiator) to produce compounds having the formula 50. Compounds useful as starting materials having the generic formula 20 are known in the art. For example, U.S. Pat. Nos. 4,528,311; 4,716,234; 4,719,248; 3,159,646; and 3,761,272 discloses olefinic benzotriazoles. U.S. Pat. No. 4,304,895 discloses polymerizable benzophenones (i.e., possess olefinic groups). FIGS. 5-8 illustrate the reactions schemes and reaction conditions for preparing compound 15 of FIG. 1, a compound similar to compound 15 of FIG. 1 but slightly differing in the linker between the photoinitiator moiety and the UV-absorber moiety, a compound similar to compound 14 of FIG. 1 but slightly differing in the linker between the photoinitiator moiety and the UV-absorber moiety, and compound 14 of FIG. 1, respectively. A person skilled in the art will understand the schemes and know how to prepare those compounds of the invention according to the teachings shown in the schemes and the examples later.

In addition, compounds of the inventions can be prepared based on the well known reactions under the conditions that are customary for ester, thioester, amide, urethane or urea formation.

The compounds of the invention can be used in the production of UV-absorbing ophthalmic lenses. In one aspect, the invention provide a method for making UV-absorbing ophthalmic lenses. The method comprises the steps of:
a. introducing into a mold a lens-forming material, wherein the lens-forming material comprises one or more tri-functional compounds described herein;
b. curing the lens-forming material to produce the lens; and
c. removing the lens from the mold.

A variety of different lens-forming materials can be used herein. The term "lens-forming material" is defined herein as any material that is capable of being polymerized using techniques known in the art. The lens-forming material can be a vinylic monomer, a prepolymer, a vinylic macromer, or any combination thereof. The tri-functional compounds described herein can be part of the lens-forming material as a vinylic monomer. For example, the lens-forming material can be composed of one or more tri-functional compounds in combination with other vinylic monomers, prepolymers, or macromers. In the alternative, the tri-functional compound can be polymerized with other monomers to produce prepolymers or macromers. The amount of tri-functional compound used in the lens-forming material can vary. In one aspect, the amount of tri-functional compound is selected such that the amount of initiator is from 0.05 to 3%, 0.5 to 5%, 0.5 to 4%, 0.5 to 3%, 0.5 to 2%, 0.5 to 1.5%, or about 1% by weight of the lens-forming material.

In one aspect, the lens-forming material comprises a prepolymer. For example, a fluid prepolymer composition comprising at least one actinically-crosslinkable or thermally-crosslinkable prepolymer can be used. In one aspect, the fluid prepolymer composition is an aqueous solution comprising at least one actinically-crosslinkable prepolymer. It is understood that the prepolymer composition can also include one or more vinylic monomers, one or more vinylic macromers, and/or one or more crosslinking agents. However, the amount of those components should be low such that the final ocular device does not contain unacceptable levels of unpolymerized monomers, macromers and/or crosslinking agents. The presence of unacceptable levels of unpolymerized monomers, macromers and/or crosslinking agents will require extraction to remove them, which requires additional steps that are costly and inefficient.

Examples of actinically crosslinkable prepolymers include, but are not limited to, a water-soluble crosslinkable poly(vinyl alcohol) prepolymer described in U.S. Pat. Nos. 5,583,163 and 6,303,687 (incorporated by reference in their entireties); a water-soluble vinyl group-terminated polyurethane prepolymer described in U.S. Patent Application Publication No. 2004/0082680 (herein incorporated by reference in its entirety); derivatives of a polyvinyl alcohol, polyethyleneimine or polyvinylamine, which are disclosed in U.S. Pat. No. 5,849,841 (incorporated by reference in its entirety); a water-soluble crosslinkable polyurea prepolymer described in U.S. Pat. No. 6,479,587 and in U.S. Published Application No. 2005/0113549 (herein incorporated by reference in their entireties); crosslinkable polyacrylamide; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635 and U.S. Pat. No. 6,492,478; branched polyalkylene glycol-urethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; crosslinkable polyallylamine gluconolactone prepolymers disclosed in International Application No. WO 2000/31150 and U.S. Pat. No. 6,472,489; and silicone-containing prepolymers are those described in commonly-owned U.S. Pat. Nos. 6,039,913, 7,091,283, 7,268,189 and 7,238,750.

In another aspect, the lens-forming material is a polymerizable composition comprising at least one hydrophilic vinylic monomer. Any hydrophilic vinylic monomer described above can be used. The polymerizable composition can further comprise one or more hydrophobic vinylic monomers, crosslinking agents, radical initiators, and other components know to a person skilled in the art. These materials typically require extraction steps.

In another aspect, the lens-forming material is a silicone-containing prepolymer. Examples of such silicone-containing prepolymers include those described in commonly-owned U.S. Pat. Nos. 6,039,913, 7,091,283, 7,268,189 and 7,238,750, 7,521,519; commonly-owned US patent application publication Nos. US 2008-0015315 A1, US 2008-0143958 A1, US 2008-0143003 A1, US 2008-0234457 A1, US 2008-0231798 A1, and commonly-owned US patent application Nos. 61/180,449 and 61/180,453; all of which are incorporated herein by references in their entireties.

In another aspect, the lens-forming material is a polymerizable composition comprising at least one silicon-containing vinylic monomer or macromer, or can be any lens formulations for making soft contact lenses. Exemplary lens formulations include without limitation the formulations of lotrafilcon A, lotrafilcon B, confilcon, balafilcon, galyfilcon, senofilcon A, and the like. A lens-forming material can further include other components, such as, a hydrophilic vinylic monomer, crosslinking agent, a hydrophobic vinylic monomer, a visibility tinting agent, photosensitizers, an antimicrobial agent, and the like.

In one aspect, the lens-forming material can be any silicone-containing vinylic monomers. Examples of preferred silicone-containing vinylic monomers include without limitation N-[tris(trimethylsiloxy)silylpropyl]-(meth)acrylamide, N-[tris(dimethylpropylsiloxy)-silylpropyl]-(meth)acrylamide, N-[tris(dimethylphenylsiloxy)silylpropyl](meth)acrylamide, N-[tris(dimethylethylsiloxy)silylpropyl](meth)acrylamide, N-(2-hydroxy-3-(3-(bis(trimethylsilyloxy)methylsilyl)propyloxy)propyl)-2-methyl acrylamide; N-(2-hydroxy-3-(3-(bis(trimethylsilyloxy)methylsilyl)propyloxy)propyl)acrylamide; N,N-bis[2-hydroxy-3-(3-(bis(trimethylsilyloxy)methylsilyl)propyloxy)propyl]-2-methyl acrylamide; N,N-bis[2-hydroxy-3-(3-(bis(trimethylsilyloxy)methylsilyl)propyloxy)propyl]acrylamide; N-(2-hydroxy-3-(3-(tris(trimethylsilyloxy)silyl)propyloxy)propyl)-2-methyl acrylamide; N-(2-hydroxy-3-(3-(tris(trimethylsilyloxy)silyl)propyloxy)propyl)acrylamide; N,N-bis[2-hydroxy-3-(3-(tris(trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl)propyloxy)propyl]acrylamide; N,N-bis[2-hydroxy-3-(3-(t-butyldimethylsilyl)propyloxy)propyl]-2-methyl acrylamide;

N,N-bis[2-hydroxy-3-(3-(t-butyldimethylsilyl)propyloxy)propyl]acrylamide; 3-methacryloxy propylpentamethyldisiloxane, tris(trimethylsilyloxy)silylpropyl methacrylate (TRIS), (3-methacryloxy-2-hydroxypropyloxy)propylbis(trimethylsiloxy)methylsilane), (3-methacryloxy-2-hydroxypropyloxy)propyltris(trimethylsiloxy)silane, 3-methacryloxy-2-(2-hydroxyethoxy)-propyloxy)propylbis(trimethylsiloxy)methylsilane, N-2-methacryloxyethyl-O-(methyl-bis-trimethylsiloxy-3-propyl)silyl carbamate, 3-(trimethylsilyl)propylvinyl carbonate, 3-(vinyloxycarbonylthio)propyl-tris(trimethyl-siloxy)silane, 3-[tris(trimethylsiloxy)silyl]-propylvinyl carbamate, 3-[tris(trimethylsiloxy)silyl]propyl allyl carbamate, 3-[tris(trimethylsiloxy)silyl]propyl vinyl carbonate, t-butyldimethyl-siloxyethyl vinyl carbonate; trimethylsilylethyl vinyl carbonate, and trimethylsilylmethyl vinyl carbonate). Most preferred siloxane-containing (meth)acrylamide monomers of formula (1) are N-[tris(trimethylsiloxy)silylpropyl]acrylamide, TRIS, N-[2-hydroxy-3-(3-(t-butyldimethylsilyl)propyloxy)propyl]acrylamide.

In other aspects, siloxane-containing vinylic monomers or macromers with ethylenically unsaturated group(s) can be used to produce a silicone hydrogel material, which are useful as lens-forming materials. Examples of such siloxane-containing vinylic monomers and macromers include without limitation monomethacrylated or monoacrylated polydimethylsiloxanes of various molecular weight (e.g., mono-3-methacryloxypropyl terminated, mono-butyl terminated polydimethylsiloxane or mono-(3-methacryloxy-2-hydroxypropyloxy)propyl terminated, mono-butyl terminated polydimethylsiloxane); dimethacrylated or diacrylated polydimethylsiloxanes of various molecular weight; vinyl carbonate-terminated polydimethylsiloxanes; vinyl carbamate-terminated polydimethylsiloxane; vinyl terminated polydimethylsiloxanes of various molecular weight; methacrylamide-terminated polydimethylsiloxanes; acrylamide-terminated polydimethylsiloxanes; acrylate-terminated polydimethylsiloxanes; methacrylate-terminated polydimethylsiloxanes; bis-3-methacryloxy-2-hydroxypropyloxypropyl polydimethylsiloxane; N,N,N',N'-tetrakis(3-methacryloxy-2-hydroxypropyl)-alpha,omega-bis-3-aminopropyl-polydimethylsiloxane; polysiloxanylalkyl(meth)acrylic monomers; siloxane-containing macromer selected from the group consisting of Macromer A, Macromer B, Macromer C, and Macromer D described in U.S. Pat. No. 5,760,100 (herein incorporated by reference in its entirety); the reaction products of glycidyl methacrylate with amino-functional polydimethylsiloxanes; hydroxyl-functionalized siloxane-containing vinylic monomers or macromers; polysiloxane-containing macromers disclosed in U.S. Pat. Nos. 4,136,250, 4,153,641, 4,182,822, 4,189,546, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, and 6,762,264 (here incorporated by reference in their entireties); polysiloxane-containing macromers disclosed in U.S. Pat. Nos. 4,259,467, 4,260,725, and 4,261,875 (herein incorporated by reference in their entireties). Di and triblock macromers consisting of polydimethylsiloxane and polyalkyleneoxides could also be of utility. For example one might use methacrylate end capped polyethyleneoxide-block-polydimethylsiloxane-block-polyethyleneoxide to enhance oxygen permeability. Suitable monofunctional hydroxyl-functionalized siloxane-containing vinylic monomers/macromers and suitable multi-functional hydroxyl-functionalized siloxane-containing vinylic monomers/macromers are commercially available from Gelest, Inc, Morrisville, Pa.

The lens-forming material, which includes one or more tri-functional compounds described herein is poured into a mold with a specific shape and size. When the ocular device is a contact lens, the lens can be produced using techniques known in the art. For example, the contact lens can be produced in a conventional "spin-casting mold," as described for example in U.S. Pat. No. 3,408,429, or by the full cast-molding process in a static form, as described in U.S. Pat. Nos. 4,347,198; 5,508,317; 5,583,463; 5,789,464; and 5,849,810.

Lens molds for making contact lenses are well known in the art. For example, a mold (for full cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with the lens-forming material.

Methods of manufacturing mold sections for cast-molding a contact lens are generally well known to those of ordinary skill in the art. The first and second mold halves can be formed through various techniques, such as injection molding or lathing. Examples of suitable processes for forming the mold halves are disclosed in U.S. Pat. Nos. 4,444,711; 4,460,534; 5,843,346; and 5,894,002, which are also incorporated herein by reference.

Virtually all materials known in the art for making molds can be used to make molds for preparing ocular lenses. For example, polymeric materials, such as polyethylene, polypropylene, polystyrene, PMMA, cyclic olefin copolymers (e.g., Topas® COC from Ticona GmbH of Frankfurt, Germany and Summit, N.J.; Zeonex® and Zeonor® from Zeon Chemicals LP, Louisville, Ky.), or the like can be used. Other materials that allow UV light transmission could be used, such as quartz glass and sapphire.

Once the lens-forming material is poured into the mold, the lens-forming material is cured (i.e., polymerized) to produce a polymeric matrix and ultimately the lens. The techniques for conducting the polymerization step will vary depending upon the selection of the lens-forming material. In one aspect, when the lens-forming material comprises a prepolymer comprising one or more actinically-crosslinkable ethylenically unsaturated groups, the mold containing the admixture can be exposed to a spatial limitation of actinic radiation to polymerize the prepolymer. In other aspects, the mold containing the lens forming material can be subjected to heat in order to cure the lens-forming material.

In other aspects, the energy used to cure the lens-forming material is in the form of rays directed by, for example, a mask or screen or combinations thereof, to impinge, in a spatially restricted manner, onto an area having a well defined peripheral boundary. For example, a spatial limitation of UV radiation can be achieved by using a mask or screen that has a transparent or open region (unmasked region) surrounded by a UV impermeable region (masked region), as schematically illustrated in FIGS. 1-9 of U.S. Pat. No. 6,627,124 (herein incorporated by reference in its entirety). The unmasked region has a well defined peripheral boundary with the unmasked region. The energy used for the crosslinking is radiation energy, UV radiation, visible light, gamma radiation, electron radiation or thermal radiation, the radiation energy preferably being in the form of a substantially parallel beam in order on the one hand to achieve good restriction and on the other hand efficient use of the energy.

In one aspect, the mold containing the lens-forming material is exposed to light having a wavelength greater than 340 nm, greater than 350 nm, greater than 360 nm, greater than 370 nm, or greater than 380 nm. Cut-off filters known in the art can be used to filter and prevent specific wavelengths of energy from contacting the mold and lens-forming material. The time the lens-forming mixture is exposed to the energy is relatively short, e.g. in less than or equal to 150 minutes, in less than or equal to 90 minutes, in less than or equal 60 minutes, less than or equal to 20 minutes, less than or equal to 10 minutes, less than or equal to 5 minutes, from 1 to 60 seconds, or from 1 to 30 seconds.

After polymerization of the lens-forming material and formation of the lens, the initiator and, if present, the linker are optionally cleaved from the tri-functional compound. In certain aspects, the removal of the initiator and optional linker "deprotects" the UV absorber component of the tri-functional compound. In other aspects, when the UV absorber component is protected with other groups (e.g., formulae VIII-X), the protecting groups can be readily cleaved. The conditions for deprotecting the UV absorber component can vary depending upon the selection of these components. By varying conditions such as temperature and pH, the initiator or other protecting groups can be cleaved to produce the active UV absorber component. The conditions described above for deprotection can be used herein to cleave the initiator and linker.

The invention further provides a UV-absorbing ophthalmic lenses incorporating therein a UV-absorbing compound of the invention.

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Abbreviations of Reagents:

DCM: Dichloromethane; TEA: Triethyl amine; D-MAP: 4-(Dimethyl amino) pyridine; DCC: N,N-Dicyclohexyl carbodiimide; HMPA: Hexamethylphosphoramide; THF: tetrahydrofuran; AIBN: 2-2-Azoiso bisbutyronitrile; NBS: N-Bromosuccinimide Example 1

This example illustrates the preparation of a tri-functional UV-absorber of the invention, UVA 1, based on the follow scheme.

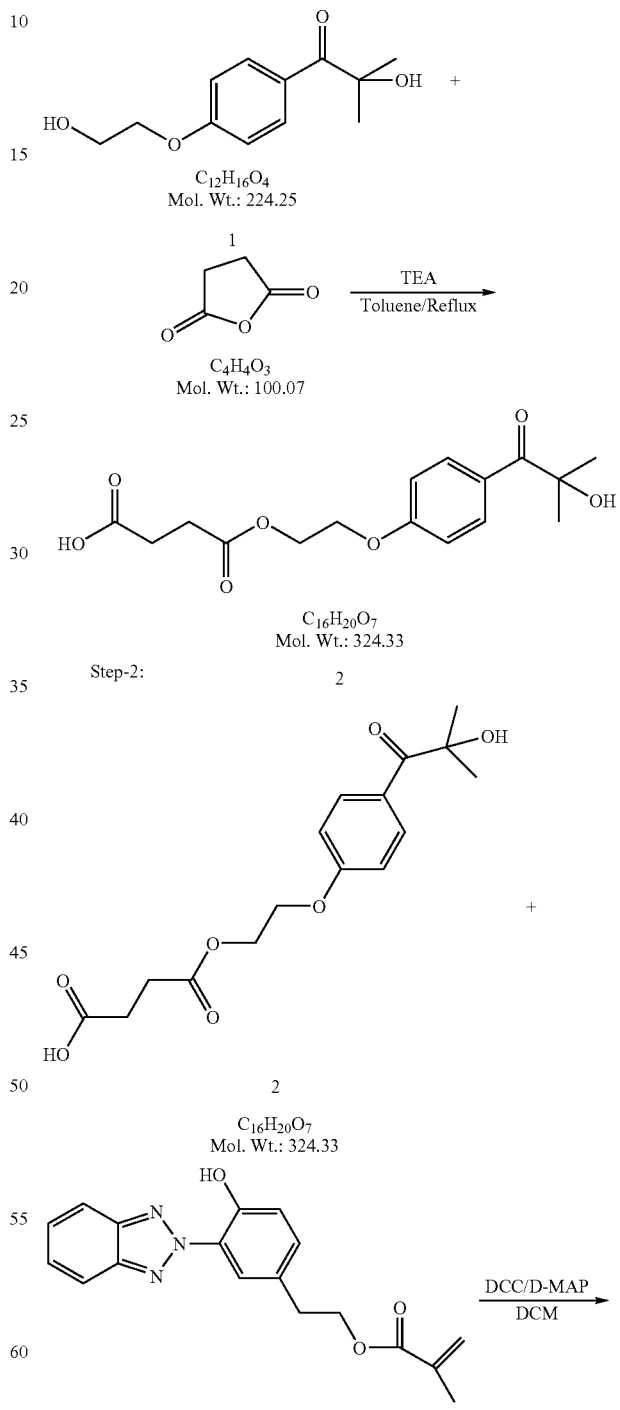

-continued

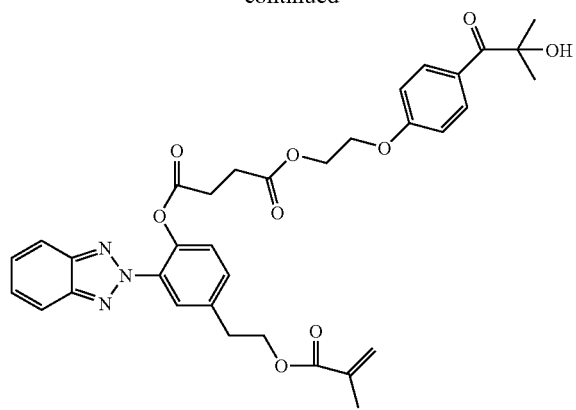

Final compound
C₃₄H₃₅N₃O₉
Mol. Wt.: 629.66

A mixture of 500 mg (2.22 mmol) 1, 245 mg (2.45 mmol) succinic anhydride, 247 mg (2.47 mmol) TEA and 10 ml toluene is refluxed for 5 hours under nitrogen atmosphere. The reaction mixture is cooled to ambient temperature, solvent is evaporated under reduced pressure, and the residue is dissolved in 10 ml of ethyl acetate and washed with 5 ml of 1N HCl. Organic layer is dried over Na₂SO₄. The solvent is removed under reduced pressure and the obtained intermediate 2, is dried under vacuum at 30° C. The results of 1H-NMR (400 MHz, DMSO-D₆) δ are: 1.35 (s, 6H), 2.47-2.54 (m, 4H), 4.27-4.26 (d, J=4 Hz, 2H), 4.370-4.358 (d, J=4.8 Hz, 2H), 5.68 (bs, 1H, OH), 7.03-7.01 (d, J=8.8 Hz, 2H), 8.22-8.19 (d, J=8.8 Hz, 2H), 12.24 (bs, 1H, COOH). The mass is determined to be 325 (M+H) by mass spectroscopy. Two peaks are observed at 212 nm and 266 nm in UV-visible absorption spectra.

A solution of 7.47 g (36.2 mmol) of DCC in 15 ml of DCM is added to a stirred mixture of 4.7 g (14.4 mmol) of 2, 4.21 g (13.04 mmol) of 3, 20 mg (0.090 mmol) of D-MAP And 35 ml of DCM at 0° C. under nitrogen atmosphere. Reaction mixture is stirred at 0° C. for 3 h, 20 ml of water is added and the mixture is extracted with DCM, the organic layer is washed with 20 ml of 1N HCl followed by brine. Organic layer is dried over Na₂SO₄, the solvent evaporated under reduced pressure, and the crude final compound, UVA 1, is purified by column chromatography on Silica (100-200 mesh) in 50% n-Hexane in ethyl acetate. The results of 1H-NMR (400 MHz, CDCl₃) δ are: 1.66 (s, 6H), 1.93 (s, 3H), 2.77-2.80 (t, d=6.8 Hz, 2H), 2.95-2.99 (t, J=6.8 Hz, 2H), 3.08-3.12 (t, J=6.8 Hz, 2H), 4.21-4.23 (m, 2H), 4.42-4.48 (m, 4H), 5.55-5.56 (t, J=1.6 Hz, 1H), 6.1 (s, 1H), 6.91-6.94 (dd, J=2.8 Hz, 2H), 7.23-7.25 (d, J=8.4 Hz, 1H), 7.34-737 (dd, J=2 Hz, 1H), 7.39-7.43 (m, 2H), 7.87-7.93 (m, 2H), 8.03-8.07 (m, 3H) MS: 630 (M+H), 652 (M+Na). Four peaks are observed at 212 nm, 272 nm, 302 nm and 590 nm in UV/Visible absorption spectra.

Example 2

This example illustrates the synthesis of a tri-functional UV-absorber of the invention, UVA 2 according to a scheme shown below:

Step 1

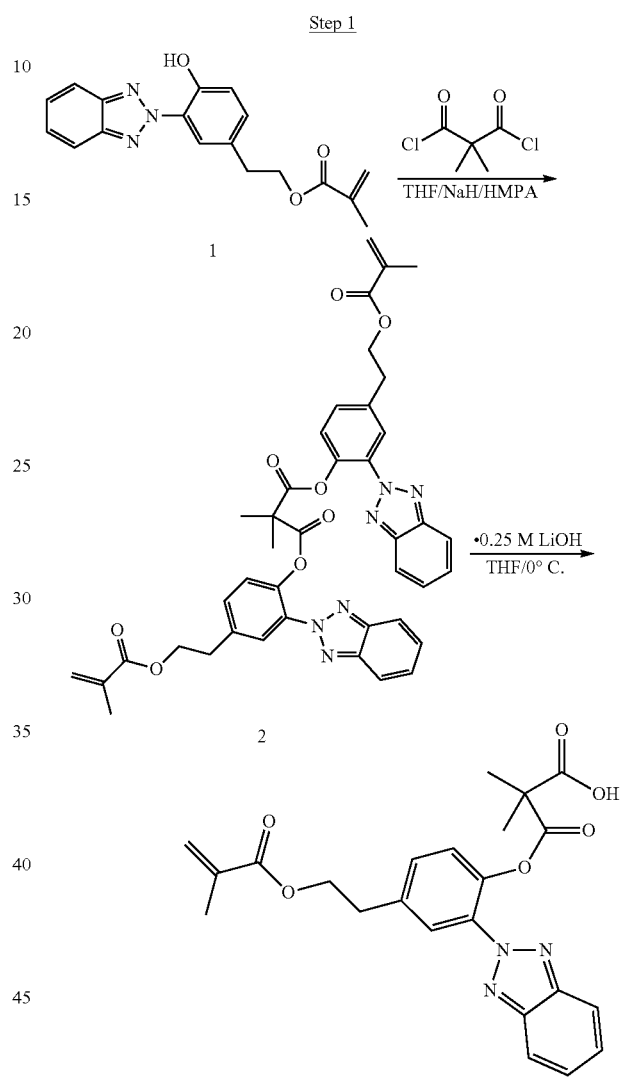

C₂₃H₂₃N₃O₆
Mol. Wt.: 437.42
Step 2   3

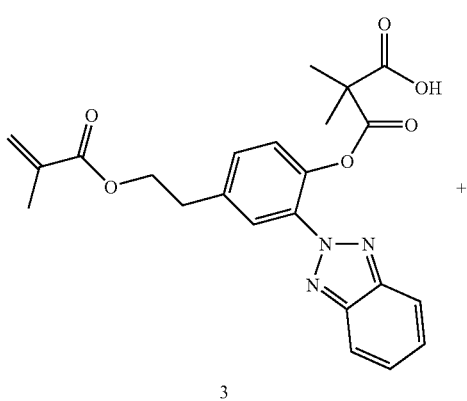

3

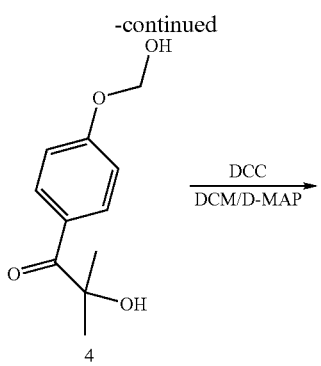

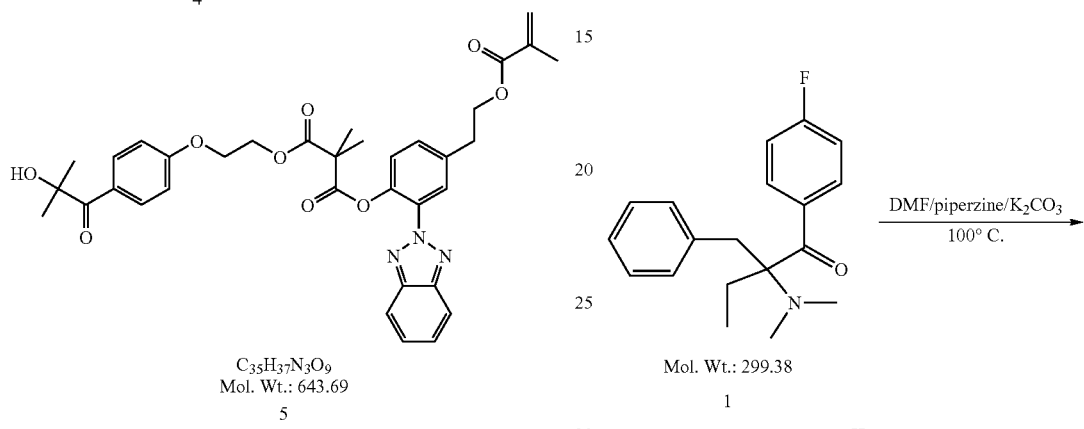

NaH 60% (0.246 g, 6 mmol) is added to a stirred solution of compound-1 (1 g, 3 mmol) and 2 ml of HMPA in 20 ml of Dry THF at 0° C. under nitrogen atmosphere. After 10 min, the solution of dimethyl malonyl chloride (3 mmol, freshly prepared form dimethyl malonic acid and oxalyl chloride) dissolved in dry-THF is added drop wise into the reaction mixture at 0° C. the reaction mixture is stirred at 0° C. for 1 h, then the reaction mixture is quenched with 1N HCl (20 ml) and extracted with DCM, dried over $Na_2SO_4$ and concentrated under reduced pressure to obtain crude intermediate (2).

Above crude (2) is dissolved in THF (20 ml) and treated with 0.2M (10 ml) of aqueous solution of LiOH and stirred overnight at ambient temperature. THF is evaporated under reduced pressure, and the resulting residue of crude intermediate (3) is diluted with water and acidified with 1N HCl (PH=3) and extracted with DCM, dried over $Na_2SO_4$, and concentrated under reduced pressure. Crude intermediate (3) thus obtained is purified by column chromatography 100-200 silica, eluted with 5% MeOH in DCM. 1H-NMR (400 MHz, $CDCl_3$) δ: 1.59 (s, 6H), 1.92 (s, 3H), 3.09-3.12 (t, 2H, J=6.4), 4.41-4.44 (t, 2H, J=6.4), 5.54-5.55 (t, 1H, J=1.6), 7.24-8 (7H, Ar—H). MS: 438 (M+H), 460 (M+Na).

A solution of 0.589 g (2.8 mmol) of DCC in 3 ml of dichloro methane is added to a stirred mixture of 0.5 g (1.14 mmol) of 3, 0.256 g (1.14 mmol) of 4, catalytic amount of D-MAP, and 5 ml of dichloro methane at 0° C. under nitrogen atmosphere. Reaction mixture is stirred at 0° C. for 3 h, 5 ml of water is added and the mixture is extracted with dichloro methane, the organic layer is washed with 5 ml of 1N HCl followed by brine. Organic layer is next dried over $Na_2SO_4$, the solvent is evaporated under reduced pressure, and the resultant crude (5), UVA 2, is purified by column chromatography on silica (100-200 mesh) in 50% n-hexane in ethyl acetate. 1H-NMR (400 MHz, $CDCl_3$) δ: 1.54 (s, 6H), 1.63 (S, 6H), 1.92 (s, 314), 3.04-3.08 (t, J=6.8 Hz, 2H), 4.20-4.23 (m, 3H), 4.37-4.4 (t, J=6.8 Hz, 2H), 4.50-4.52 (t, J=4.8 Hz, 2H), 5.54-5.55 (t, J=1.6 Hz, 1H), 6.09 (s, 1H), 6.87-6.91 (m, 2H), 7.16-7.21 (m, 2H), 7.39-7.44 (m, 2H), 7.87-7.91 (m, 2H), 7.99 (s, 1H), 8.04-8.08 (m, 2H). MS: M+H (644), M+Na (666). Three peaks are observed at 218 nm, 266 nm and 302 nm in UV Visible absorption spectra.

Example 3

This example illustrates the synthesis of a tri-functional UV-absorber of the invention, UVA 3 according to a scheme shown below:

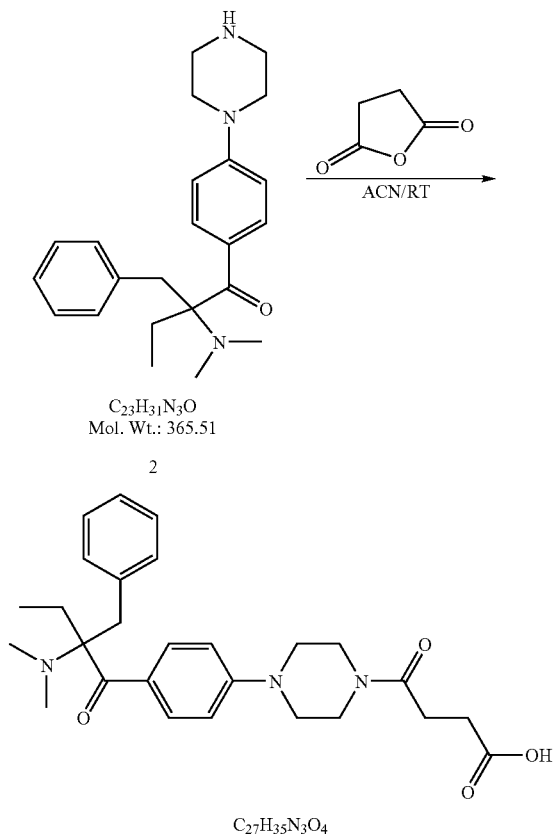

-continued

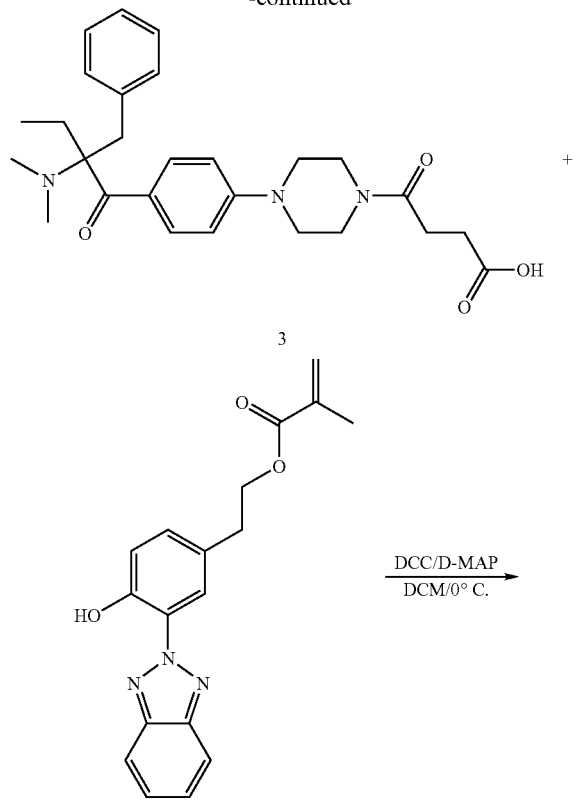

Starting fluoro compound (p-fluro acetaophenone derivative 1) is prepared according to the procedures described in U.S. Pat. No. 5,554,663 (herein incorporated by reference in its entirety).

Intermediate-2 is prepared as follows. p-Fluoro acetophenone derivative 1 (5 g, 0.017 mol), piperizine (2.0 g, 0.033 mol) and potassium carbonate (6.9 g, 0.05 mol) are dissolved in 50 ml dry DMF and reflux for 24 h under nitrogen atmosphere. After complete consumption of starting material (the progress of the reaction is monitored by TLC), the reaction is cooled to room temperature and after the solvent (DMF) is evaporated, the residue is dissolved in dichloromethane and washed with water (3×20 mL). The organic layer is washed with brine and dried over anhydrous sodium sulphate. The crude product obtained after evaporation is purified by column chromatography using 5% methanol in dichloromethane (100-200 mesh silica gel).

Intermediate 2 (5 g, 0.01369 mol) and succinic anhydride (1.37 g, 0.0137) dissolved in acetonitrile (50 ml) is stirred at room temperature for 1 hr., then the solvent is evaporated under vacuum to yield compound 3 as yellow residue. It is used for the next step without further purification.

DCC (6.2 g, 0.05 mol) in DCM (20 ml) is added to the stirred mixture of compound 3 (5.6 g, 0.012 mol), Benzotrizole derivative (4.28 g, 0.013 mol) and catalytic amount of D-MAP in DCM (40 ml) at 0° C. under nitrogen. Mixture is stirred at 0° C. for 6 hrs. 50 ml of water is added and the mixture is extracted with dichloro methane, the organic layer is washed with 30 ml of 1N HCl followed by brine. The organic layer is dried over $Na_2SO_4$, the solvent is evaporated under reduced pressure, and the crude target compound 4, UVA 3, is purified by column chromatography on Silica (100-200 mesh) followed by elution with 30% n-hexane in ethyl acetate. 1H-NMR (400 MHz, $CDCl_3$) δ 0.58-0.62 (t, J=7.6 Hz, 3H), 1.17-1.18 (m, 2H), 1.73-1.80 (m, 2H), 1.85 (s, 4H), 2.28 (s, 6H), 2.65-2.68 (t, J=6.8 Hz, 2H), 2.93-2.97 (t, J=7.2 Hz, 2H), 3.01-3.15 (m, 4H), 3.24 (s, 4H), 3.52-3.54 (t, J=4.8 Hz, 2H), 3.7 (t, J=4.8 Hz, 2H), 4.35 (t, J=6.8 Hz, 2H), 5.48 (s, 1H), 6.03 (s, 1H), 6.72 (d, J=9.2 Hz, 2H), 7.09-7.11 (m, 4H), 7.22-7.24. (d, J=8.4 Hz, 1H), 7.30-7.33 (dd, J=2 Hz, 1H), 7.35-7.38 (m, 2H), 7.84-7.88 (m, 2H), 8.27-8.30 (d, J=8.8 Hz, 2H). MS: M+H (771.8). Three peaks are observed at 216 nm, 284 nm and 302 nm in UV visible spectra Example 4

This example illustrates the synthesis of a tri-functional UV-absorber of the invention, UVA 4 according to a scheme shown below:

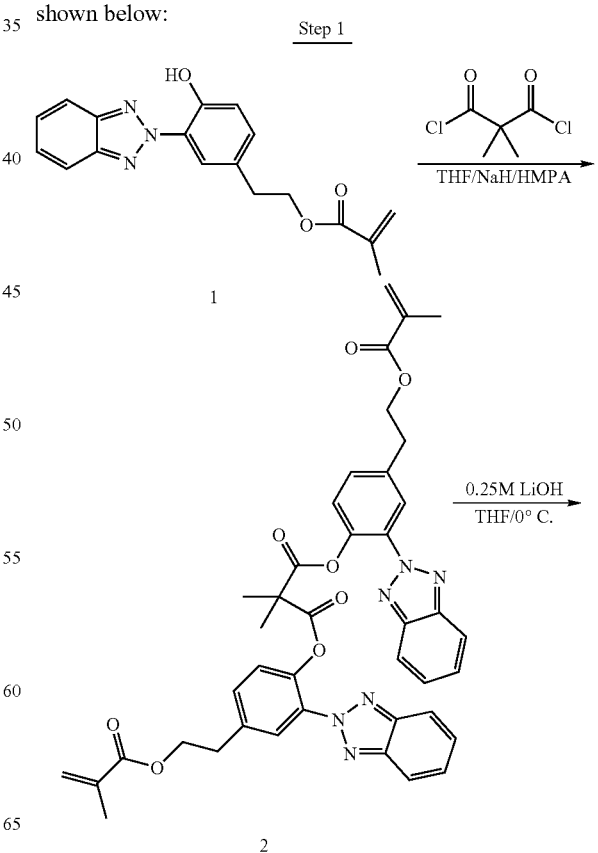

-continued

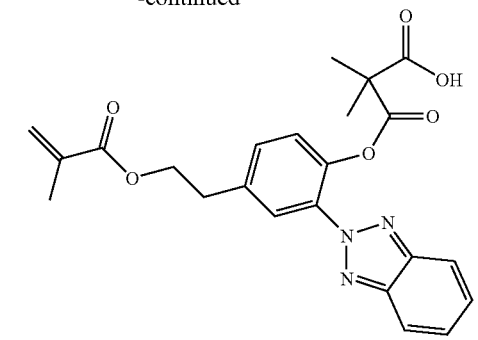

C$_{23}$H$_{23}$N$_3$O$_6$
Mol. Wt.: 437.45

3

Step 2

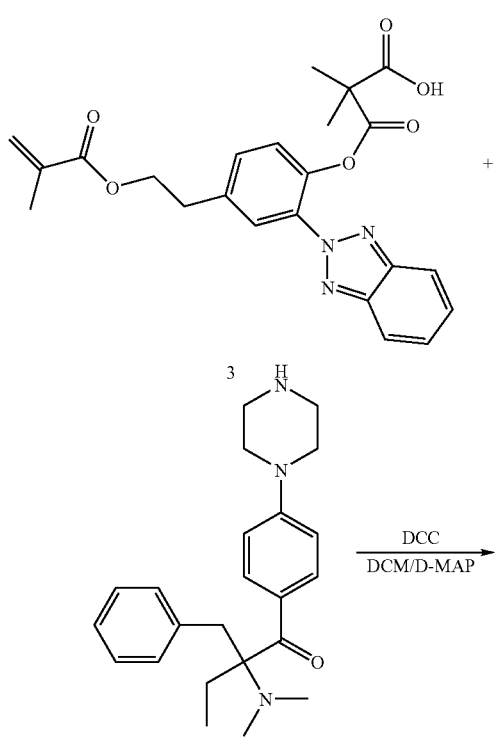

Preparation of Compound-3: NaH 60% (0.246 g, 6 mmol) is added to a stirred solution of compound-1 (1 g, 3 mmol) and 2 ml of HMPA in 20 ml of Dry THF added at 0° C. under nitrogen atmosphere. After 10 min, the solution of dimethyl malonyl chloride (3 mmol, freshly prepared form dimethyl malonic acid and oxalyl chloride) dissolved in dry-THF is added dropwise into the reaction mixture at 0° C. The reaction mixture is stirred at 0° C. for 1 h, then the reaction mixture is quenched with 1N HCl (20 ml) and extracted with DCM, dried over Na$_2$SO$_4$ and concentrated under reduced pressure to obtain crude product (2).

Above crude compound (2) is dissolved in THF (20 ml) and treated with 0.2M aqueous solution of LiOH over night at ambient temperature. THF is evaporated under reduced pressure, then the crude residue is diluted with water and acidified with 1N HCl (PH=3) and extracted with DCM, dried over Na$_2$SO$_4$, concentrated under reduced pressure, and the resulting crude intermediate (3) is purified by column chromatography using 100-200 silica, 5% MeOH in DCM as eluting agent. 1H-NMR (400 MHz, CDCl$_3$) δ: 1.59 (s, 6H), 1.92 (s, 3H), 3.09-3.12 (t, 2H, J=6.4), 4.41-4.44 (t, 2H, J=6.4), 5.54-5.55 (t, 1H, J=1.6), 7.24-8 (7H, Ar—H). MS: 438 (M+H), 460 (M+Na).

A solution of 5.7 g (0.00277 mol) of DCC in 20 ml of dichloro methane is added to a stirred mixture of 4.8 g (0.01108 mol) of 3, 2.83 g (0.0077 mol) of 4, catalytic amount of D-MAP and 40 ml of dichloro methane at 0° C. under nitrogen atmosphere. Reaction mixture is stirred at 0° C. for 6 h, 50 ml of water is added and the mixture is extracted with dichloro methane, the organic layer is washed with 30 ml of 1N HCl followed by brine. Organic layer is dried over Na$_2$SO$_4$, the solvent is evaporated under reduced pressure, the crude target compound, DP-UVA 4, is purified by column chromatography on silica (100-200 mesh) in 50% n-Hexane in ethyl acetate. 1H-NMR (400 MHz, CDCl$_3$) δ: 0.63-0.67 (t, J=7.2 Hz, 3H), 1.57 (s, 8H), 2.00 (s, 3H), 2.33 (s, 3H), 3.07-3.20 (m, 8H), 3.45-3.46 (m, 4H), 4.39-4.42 (t, J=6.8 Hz, 2H), 5.53 (m, 1H), 6.07 (s, 1H), 6.67-6.70 (d, J=9.2 Hz, 2H), 7.12-7.22 (m, 8H), 7.38-7.46 (m, 2H), 7.88-7.91 (m, 2H), 8.30-8.33 (d, J=9.2 Hz, 2H). MS: M+H (785.5), M+Na (807.4). Five peaks are observed at 302 nm, 350 nm, 482 nm, 530 nm and 560 nm in UV visible spectra Example 5

This example illustrates the synthesis of a tri-functional UV-absorber of the invention, UVA 5 according to a scheme show below:

Step: 1

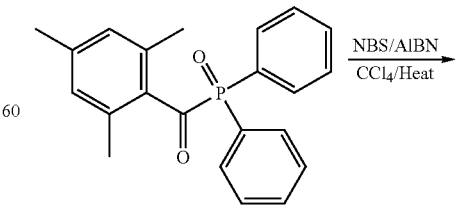

Darocure-TPO, Mw: 348.13

1

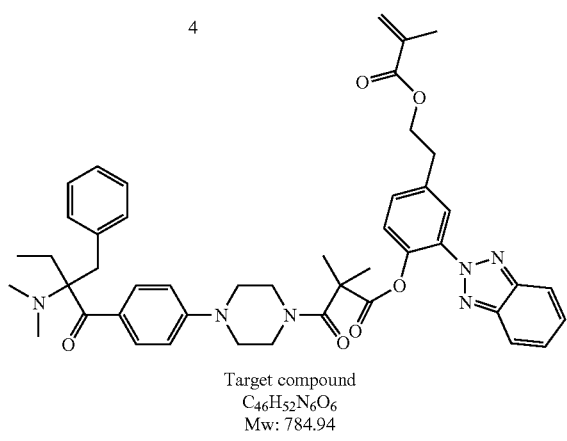

Target compound
C$_{46}$H$_{52}$N$_6$O$_6$
Mw: 784.94

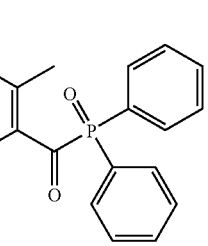
Mw: 426.04
2
Step: 2
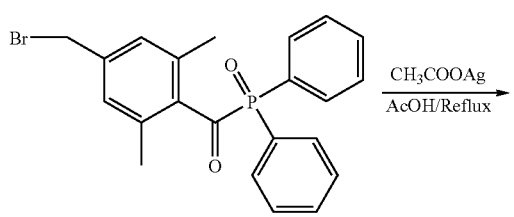
2
Exact Mass: 426.04
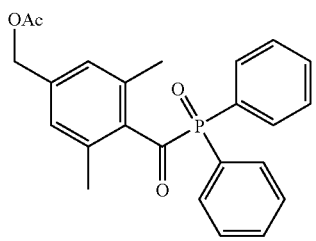
3
Exact Mass: 406.13
Step: 3
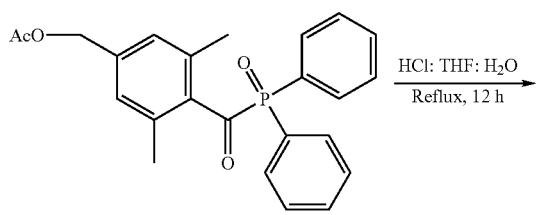
3
Exact Mass: 406.13
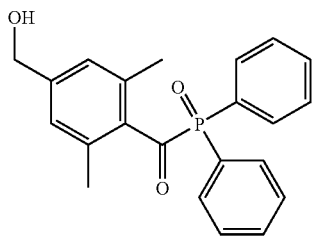
4
Exact Mass: 364.12
Step 4:
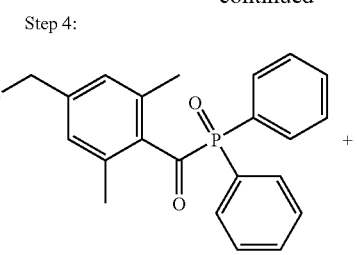
Exact Mass: 364.12
4
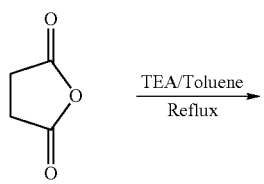
Exact Mass: 100.02
5
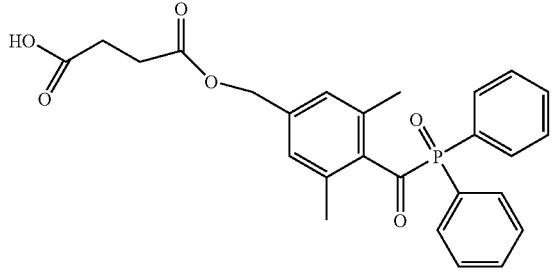
Exact Mass: 464.14
6
Step 5:
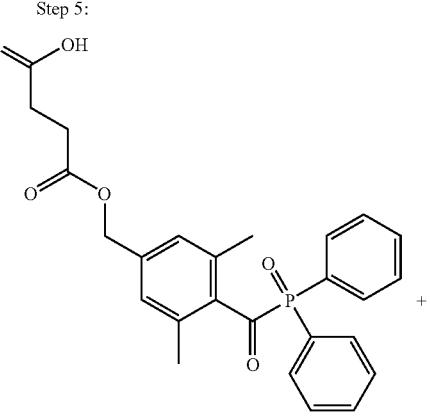
Exact Mass: 464.14
6

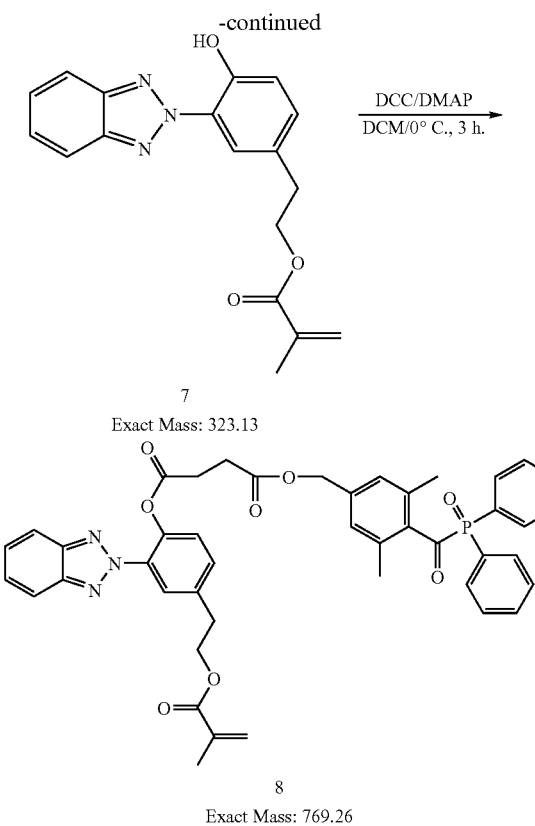

7
Exact Mass: 323.13

8
Exact Mass: 769.26

A mixture of 5 g (14.3 mmol) of compound 1, 3.55 g (20.09 mmol) of N-Bromosuccinimide, 0.05 g of AIBN and 30 ml of tetrachloromethane is refluxed for 5 h under Nitrogen atmosphere. The reaction mixture is filtered after cooling. The filtrate evaporated and dried to obtain compound-2 (8.4 g crude), crude TLC shows closure multiple spots. Without further purification the material is taken for next step.

A mixture of 19.8 mmol of compound 2, 3.64 g (21.8 mmol) of silver acetate and 85 ml of glacial acetic acid is refluxed for 3 h. The mixture is filtered and 500 ml of water is added to the filtrate and mixture is extracted with 150 ml of DCM (3 times). Combined organic layer is washed with 100 ml of water (3 times), dried over $Na_2SO_4$ and the solvent is removed under reduced pressure. Crude product is purified by column chromatography (25% EtOAc in Hexane). The compound-3 is obtained after solvent evaporation. 1H-NMR (400 MHz, $CDCl_3$) δ: 2.05 (s, 6H), 2.35 (s, 3H), 5.1 (s 2H), 6.99 (s, 2H), 7.49-7.60 (m, 6H), 7.97-8.02 (m, 4H). MS: 407 (M+H), 429 (M+Na).

A mixture of 2 g (4.922 mmol) of compound 3.28, 12 ml THF, 2.81 ml HCl, 14.06 ml of water (0.2:2:1) is refluxed for over night. THF is removed under reduced pressure and 10 ml water is added and the mixture is extracted with 15 ml of DCM (3 times), combined organic layer are washed with 15 ml of water (3 times), the organic layer is dried over $Na_2SO_4$, and the solvent is evaporated. The crude product is purified by column chromatography (2% MeOH in DCM). After drying, compound 4 is obtained. 1H-NMR: (400 MHz, $CDCl_3$) δ: 2.05 (s, 6H), 2.74 (bs, 1H, OH), 4.59 (s 2H), 6.99 (s, 2H), 7.49-7.60 (m, 6H), 7.97-8.02 (m, 4H). MS: 365 (M+H), 387 (M+Na).

A mixture of 4 g (10.977 mmol) 4, 1.20 g (12.0747 mmol) succinic anhydride 5, 1.22 g (12.0474 mmol), triethyl amine and 40 ml of dry toluene is refluxed for 5 h under nitrogen atmosphere and then cooled to ambient temperature. The solvent is evaporated under reduced pressure, the residue is dissolved in 50 ml of ethyl acetate and washed with 20 ml of 1N HCl. Organic layer is dried over $Na_2SO_4$. The solvent is removed under reduced pressure and the obtained product 6 is dried under vacuum at 30° C. 1H-NMR: (400 MHz, $CDCl_3$) δ: 2.05 (s, 6H), 2.58-2.56 (t, J=5.6 Hz, 4H), 5.08 (s 2H), 6.99 (s, 2H), 7.49-7.60 (m, 6H), 7.97-8.02 (m, 4H). MS: 465 (M+H), 487 (M+Na).

A solution of 5.44 g (26.37 mmol) of DCC in 50 ml of dichloro methane is added to a stirred mixture of 4.9 g (10.55 mmol) of 6, 3.411 g (10.55 mmol) of 7, 50 mg (0.225 mmol) of D-MAP and 50 ml of Dichloro methane at 0° C. under nitrogen atmosphere. Reaction mixture is stirred at 0° C. for 3 hours. 20 ml of water is added and the mixture is extracted with dichloro methane. The organic layer is washed with 20 ml of 1N HCl followed by brine. The organic layer is dried over $Na_2SO_4$, the solvent is evaporated under reduced pressure and the crude compound is purified by column chromatography on Silica (100-200 mesh) in 2% acetone in DCM. 1H-NMR (400 MHz, $CDCl_3$) δ: 1.73 (s, 3H), 1.89 (s, 6H), 2.69-2.72 (t, J=7.2 Hz, 2H), 2.85-2.89 (t, J=6.0 Hz, 2H), 3.07-3.10 (t, J=6.4 Hz, 2H), 4.35-4.38 (t, J=6.4 Hz, 2H), 5.01 (s, 1H), 5.99 (s, 1H), 7.00 (s, 1H), 7.28-7.30 (d, J=8.4 Hz, 1H), 7.48-7.50 (m, 3H), 7.51-7.62 (m, 4H), 7.63-7.70 (m, 2H), 7.86-7.99 (m, 4H), 8.03-8.07 (m, 2H), 8.08 (s, 1H). MS: 770 (M+H). Three peaks are observed at 218 nm, 296 nm and 380 respectively in UV/Visible absorption spectra.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:
1. A compound of formula I

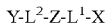

wherein
Z is the ultraviolet absorber and is a divalent radical of formula (1a) or (1c)

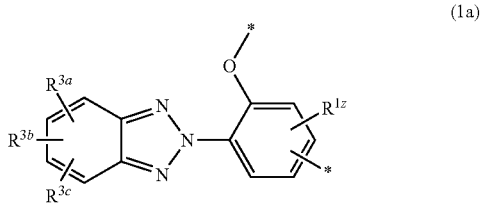

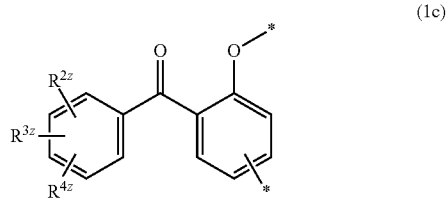

in which $R^{3a}$, $R^{3b}$, $R^{3c}$, $R^{2z}$, $R^{3z}$, $R^{4z}$, and $R^{1z}$, independent of another, are hydrogen, halogen, a $C_1$-$C_{12}$ linear or branched alkyl group, a $C_1$-$C_{12}$ linear or branched alkoxy group, or a $C_6$-$C_{24}$ aryl or substituted aryl group;

X is the polymerization initiator and is a monovalent radical comprising a polymerization initiator moiety selected from the group consisting of phosphine oxide

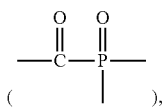

a peroxide group, an azide group, an α-hydroxyketone, and an α-aminoketone;

Y is the ethenically unsaturated group and is a monovalent radical of formula (2)

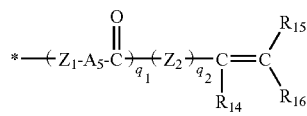

(2)

in which $Z_1$ and $Z_2$ independent of each other are a covalent bond, a linear or branched $C_1$-$C_{12}$ alkylene divalent radical, a linear or branched $C_1$-$C_{12}$ alkylene divalent radical having one or more hydroxyl groups, a radical of —$(CH_2CH_2O)_d$—$CH_2CH_2$— in which d is an integer of 1 to 10, unsubstituted phenylene divalent radical, $C_1$-$C_4$ alkyl or $C_1$-$C_4$ alkoxy substituted phenylene divalent radical, $C_7$-$C_{12}$ aralkylene divalent radical,

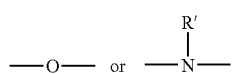

in which R' is H or $C_1$-$C_8$ alkyl; $A_5$ is a covalent bond,

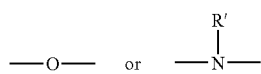

in which R' is H or $C_1$-$C_8$ alkyl; $q_1$ and $q_2$ independent of each other are an integer of 0 or 1; $R_{14}$ is hydrogen, $C_1$-$C_4$ alkyl or halogen; $R_{15}$ and $R_{16}$ independent of each other are hydrogen, $C_1$-$C_4$ alkyl, phenyl, carboxy, halogen, or a radical of

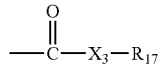

in which $X_3$ is

as defined above or —S— and $R_{17}$ is $C_1$-$C_{12}$ alkyl, $C_1$-$C_{12}$ hydroxyalkyl, $C_1$-$C_{12}$ aminoalkyl, alkylaminoalkyl having up to 12 carbon atoms, or dialkylaminoalkyl having up to 12 carbon atoms; and $L^1$ and $L^2$ independently of each other are a covalent bond or a linker.

2. The compound of claim 1, wherein the polymerization initiator comprises a phosphine oxide, a peroxide group, or an azide group.

3. The compound of claim 1, wherein the polymerization initiator comprises a monovalent radical of formula IIa, IIb or XI

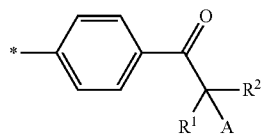

IIa

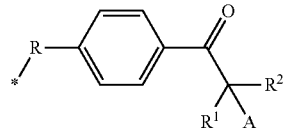

IIb

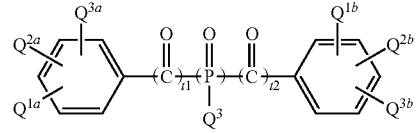

XI wherein:
(1) R is oxygen, nitrogen, a linear or branched $C_1$-$C_{12}$ alkylene divalent radical, a divalent radical of —$OCH_2CH_2O$—, a divalent radical of

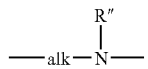

in which $R''$ is hydrogel or a $C_1$-$C_{12}$ alkyl radical and alk is $C_1$-$C_{12}$ alkylene divalent radical, or combinations thereof, $R^1$ and $R^2$ are, independently, hydrogen, a $C_1$-$C_{12}$ linear or branched alkyl group, a $C_6$-$C_{24}$ aryl or substituted aryl group, a $C_7$-$C_{24}$ aralkyl group;

(2) A is a monovalent radical selected from the group consisting of a hydroxyl group, a $C_1$-$C_{12}$ alkoxy group, a $C_6$-$C_{24}$ aryloxy group, a primary amino group, secondary amino group, and tertiary amino group; and (3) t1 and t2 independent of each other are 0 or 1 provided that at least one of t1 and t2 is 1, one of $Q^{1a}$ and $Q^{1b}$ is a covalent bond and the other is hydrogen, $C_1$-$C_6$ linear or branched alkyl group, or $C_1$-$C_6$ linear or branched alkoxy group, $Q^{2a}$, $Q^{2b}$, $Q^{3a}$, $Q^{3b}$ independently of one another hydrogen are $C_1$-$C_{12}$ linear or branched alkyl group, or $C_1$-$C_{12}$ linear or branched alkoxy group.

4. The compound of claim 1, wherein the polymerization initiator comprises a monovalent radical of formula III or IVa or b

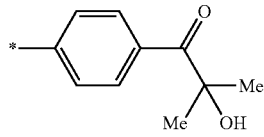
III

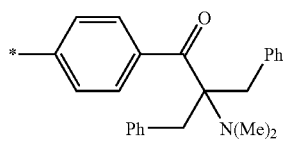
IVa

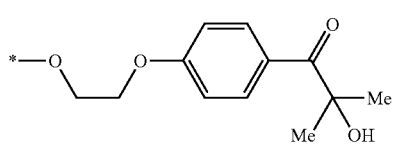
IVb in which Ph is phenyl group and Me is methyl group.

5. The compound of claim 1, wherein the polymerization initiator comprises a monovalent radical of formula XII

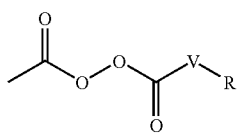
XII wherein V is a covalent bond or oxygen, and R is a $C_1$-$C_{20}$ linear or branched alkyl group or phenyl.

6. The compound of claim 3, wherein $L^1$ and $L^2$ independent of each other are a covalent bond or a linker of a silicon group, a carbonyl group, a dicarbonyl group, an alkylene group, an alkylene oxide group, an alkylene amine group, or any combination thereof.

7. The compound of claim 3, wherein $L^1$ and $L^2$ independent of each other are a covalent bond or a divalent radical of

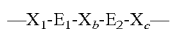

in which:

$X_a$ is a covalent bond, carbonyl

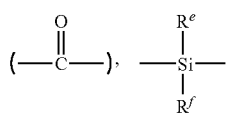

in which $R^e$ and $R^f$ independently of each other are a $C_1$-$C_8$-alkyl, phenyl or a $C_1$-$C_4$ alkyl- or $C_1$-$C_4$- alkoxy-substituted phenyl, a divalent radical of —($R^aO$)$_n$— in which $R^a$ is a linear or branched $C_1$-$C_{12}$-alkylene and n is from 1 to 10,

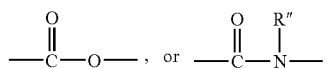

in which R" is H or $C_1$-$C_8$ alkyl;

$E_1$ and $E_2$ independently of each other are a covalent bond, a divalent radical of —($R^aO$)$_n$— in which $R^a$ and n are defined above,

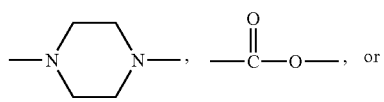

in which R" is H or $C_1$-$C_8$ alkyl, a $C_1$ to $C_{12}$ linear or branched alkylene divalent radical, a cycloalkyl diradical with up to 40 carbon atoms, an alkylcycloalkyl diradical with up to 40 carbon atoms, an alkylaryl diradical with up to 40 carbon atoms, an arylalkylene divalent radical with up to 40 carbon atoms, or a dicarbonyl group having the formula —C(O)$L^3$C(O)— in which $L^3$ is a $C_1$ to $C_{12}$ linear or branched alkylene divalent radical or —($R^{e1}$—O)$_{w1}$—($R^{e2}$—O)$_{w2}$—($R^{e3}$—O)$_{w3}$—, wherein $R^{e1}$, $R^{e2}$, and $R^{e3}$ independently of one another are a linear or branched $C_1$-$C_4$-alkylene and w1, w2 and w3 independently of one another are a number from 0 to 20 provided that the sum of (w1+w2+w3) is 1 to 60; and $X_b$ and $X_c$ independently of each other are a covalent bond,

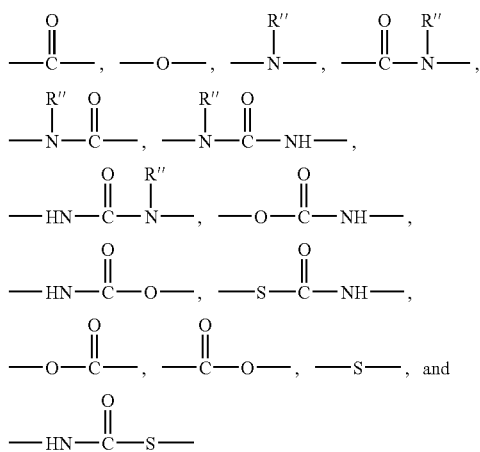

in which R" is defined above.

8. The compound of claim 7, wherein the compound is defined by the formula V

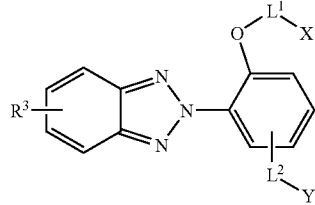

V wherein $R^3$ is hydrogen, halogen, a $C_1$-$C_{12}$ linear or branched alkyl group, a $C_1$-$C_{12}$ linear or branched alkoxy group, or a $C_6$-$C_{24}$ aryl or substituted aryl group.

9. The compound of claim 8, wherein X is a monovalent radical of the formula VI

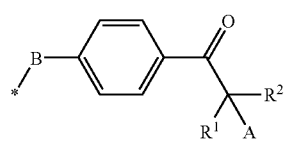

VI wherein: $R^1$ and $R^2$ are, independently, hydrogen, a $C_1$-$C_{12}$ linear or branched alkyl group, a $C_6$-$C_{24}$ aryl or substituted aryl group, a $C_7$-$C_{24}$ aralkyl group;

A is a hydroxyl group, a $C_1$-$C_{12}$ alkoxy group, a $C_6$-$C_{24}$ aryloxy group, or an amino group; and B is a silicon group, a carbonyl group, a dicarbonyl group, a $C_1$-$C_{12}$ linear or branched alkylene group, a $C_1$-$C_{12}$ linear or branched alkylene oxide group, a $C_1$-$C_{12}$ linear or branched alkylene amine group, or any combination thereof.

10. The compound of claim 7, wherein the compound has the formula VII

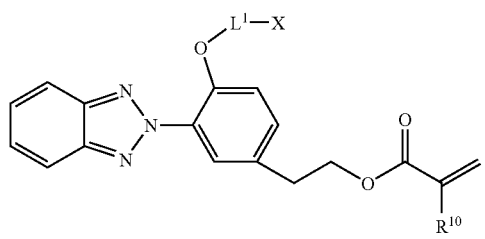

VII wherein $R^{10}$ is hydrogen or methyl.

11. The compound of claim 10, wherein $L^1$ is a divalent radical of the formula

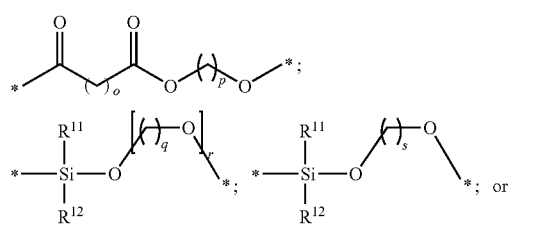

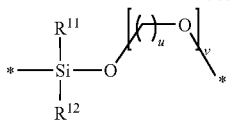

wherein o, p, q, r, s, u, and v are, independently, an integer from 1 to 5; and $R^{11}$ and $R^{12}$ independently of each other are hydrogen or a $C_1$-$C_{12}$ linear or branched alkyl group.

12. An ophthalmic lens comprising a polymer which is the copolymerization product of a polymerizable composition including one or more vinylic monomers and/or macromers and at least one compound of formula I $$Y\text{-}L^2\text{-}Z\text{-}L^1\text{-}X \qquad \text{I}$$

wherein

Z is a divalent radical of formula (1a) or (1c)

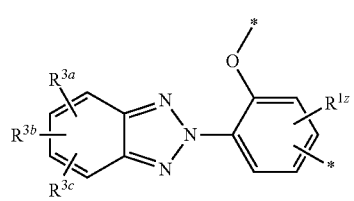

(1a)

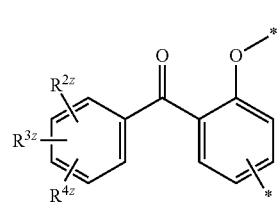

(1c)

in which $R^{3a}$, $R^{3b}$, $R^{3c}$, $R^{2z}$, $R^{3z}$, $R^{4z}$, and $R^{1z}$, independent of another, are hydrogen, halogen, a $C_1$-$C_{12}$ linear or branched alkyl group, a $C_1$-$C_{12}$ linear or branched alkoxy group, or a $C_6$-$C_{24}$ aryl or substituted aryl group;

X is a monovalent radical comprising a polymerization initiator moiety selected from the group consisting of phosphine oxide

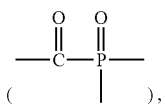

a peroxide group, an azide group, an α-hydroxyketone, or an α-aminoketone;

Y is a monovalent radical of formula (2)

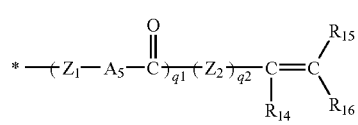

(2)

in which $Z_1$ and $Z_2$ independent of each other are a covalent bond, a linear or branched $C_1$-$C_{12}$ alkylene divalent radical, a linear or branched $C_1$-$C_{12}$ alkylene divalent radical having one or more hydroxyl groups, a radical of —$(CH_2CH_2O)_d$—$CH_2CH_2$— in which d is an integer of 1 to 10, unsubstituted phenylene divalent radical, $C_1$-$C_4$ alkyl or $C_1$-$C_4$ alkoxy substituted phenylene divalent radical, $C_7$-$C_{12}$ aralkylene divalent radical,

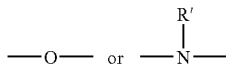

in which R' is H or $C_1$-$C_8$ alkyl; $A_5$ is a covalent bond,

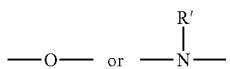

in which R' is H or $C_1$-$C_8$ alkyl; $q_1$ and $q_2$ independent of each other are an integer of 0 or 1; $R_{14}$ is hydrogen, $C_1$-$C_4$ alkyl or halogen; $R_{15}$ and $R_{16}$ independent of each other are hydrogen, $C_1$-$C_4$ alkyl, phenyl, carboxy, halogen, or a radical of

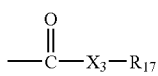

in which $X_3$ is

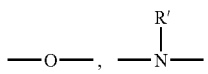

as defined above or —S— and $R_{17}$ is $C_1$-$C_{12}$ alkyl, $C_1$-$C_{12}$ hydroxyalkyl, $C_1$-$C_{12}$ aminoalkyl, alkylaminoalkyl having up to 12 carbon atoms, or dialkylaminoalkyl having up to 12 carbon atoms; and $L^1$ and $L^2$ independently of each other are a covalent bond or a linker.

13. The ophthalmic lens of claim 12, wherein the polymerization initiator moiety comprises a monovalent radical of formula IIa, IIb or XI

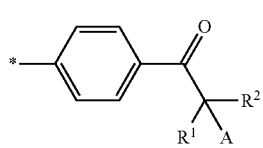

IIa

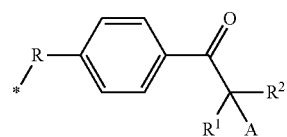

IIb

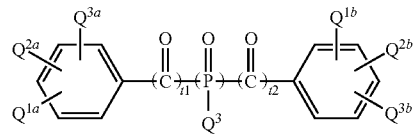

XI wherein:
(1) R is oxygen, nitrogen, a linear or branched $C_1$-$C_{12}$ alkylene divalent radical, a divalent radical of —$OCH_2CH_2O$—, a divalent radical of

in which $R''$ is hydrogel or a $C_1$-$C_{12}$ alkyl radical and alk is $C_1$-$C_{12}$ alkylene divalent radical, or combinations thereof, $R^1$ and $R^2$ are, independently, hydrogen, a $C_1$-$C_{12}$ linear or branched alkyl group, a $C_6$-$C_{24}$ aryl or substituted aryl group, a $C_7$-$C_{24}$ aralkyl group;
(2) A is a monovalent radical selected from the group consisting of a hydroxyl group, a $C_1$-$C_{12}$ alkoxy group, a $C_6$-$C_{24}$ aryloxy group, a primary amino group, secondary amino group, and tertiary amino group; and
(3) t1 and t2 independent of each other are 0 or 1 provided that at least one of t1 and t2 is 1, one of $Q^{1a}$ and $Q^{1b}$ is a covalent bond and the other is hydrogen, $C_1$-$C_6$ linear or branched alkyl group, or $C_1$-$C_6$ linear or branched alkoxy group, $Q^{2a}$, $Q^{2b}$, $Q^{3a}$, $Q^{3b}$ independently of one another hydrogen are $C_1$-$C_{12}$ linear or branched alkyl group, or $C_1$-$C_{12}$ linear or branched alkoxy group.

14. The ophthalmic lens of claim 13, wherein $L^1$ and $L^2$ independent of each other are a covalent bond or a divalent radical of —$X_a$-$E_1$-$X_b$-$E_2$-$X_c$— in which:
$X_a$ is a covalent bond, carbonyl

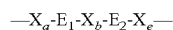

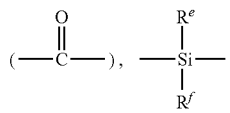

in which $R^e$ and $R^f$ independently of each other are a $C_1$-$C_8$-alkyl, phenyl or a $C_1$-$C_4$ alkyl- or $C_1$-$C_4$-alkoxy-substituted phenyl, a divalent radical of —$(R^aO)_n$— in which $R^a$ is a linear or branched $C_1$-$C_{12}$-alkylene and n is from 1 to 10,

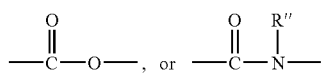

in which $R''$ is H or $C_1$-$C_8$ alkyl;
$E_1$ and $E_2$ independently of each other are a covalent bond, a divalent radical of —$(R^aO)_n$— in which $R^a$ and n are defined above,

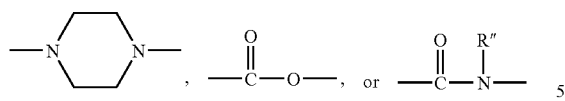

in which R" is H or $C_1$-$C_8$ alkyl, a $C_1$ to $C_{12}$ linear or branched alkylene divalent radical, a cycloalkyl diradical with up to 40 carbon atoms, an alkylcycloalkyl diradical with up to 40 carbon atoms, an alkylaryl diradical with up to 40 carbon atoms, an arylalkylene divalent radical with up to 40 carbon atoms, or a dicarbonyl group having the formula —C(O)$L^3$C(O)— in which $L^3$ is a $C_1$ to $C_{12}$ linear or branched alkylene divalent radical or —($R^{e1}$—O)$_{w1}$—($R^{e2}$—O)$_{w2}$—($R^{e3}$—O)$_{w3}$—, wherein $R^{e1}$, $R^{e2}$, and $R^{e3}$ independently of one another are a linear or branched $C_1$-$C_4$-alkylene and w1, w2 and w3 independently of one another are a number from 0 to 20 provided that the sum of (n+m+p) is 1 to 60; and $X_b$ and $X_c$ independently of each other are a covalent bond,

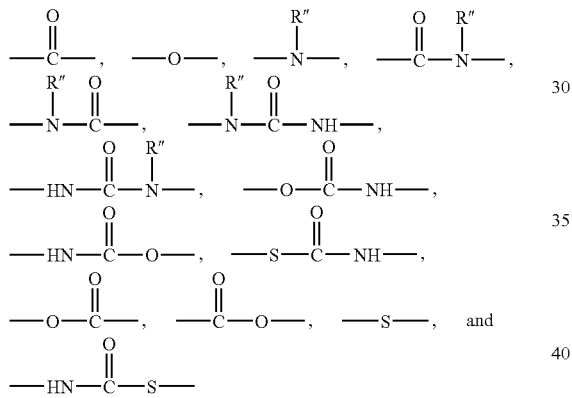

in which R" is defined above.

15. A method for making UV-absorbing ophthalmic lenses, comprising the steps of:

a. introducing into a mold a lens-forming material, wherein the lens-forming material comprises one or more vinylic monomers and/or macromers and at least one compound of formula I

Y-$L^2$-Z-$L^1$-X      I wherein

Z is a divalent radical of formula (1a) or (1c)

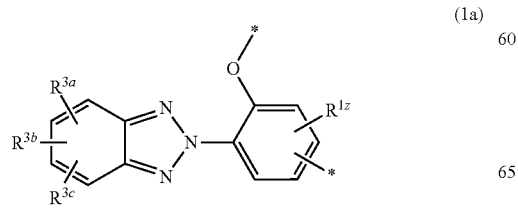

(1a)

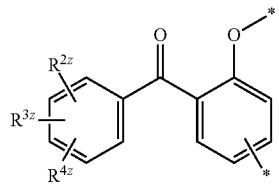

(1c)

in which $R^{3a}$, $R^{3b}$, $R^{3c}$, $R^{2z}$, $R^{3z}$, $R^{4z}$, and $R^{1z}$, independent of another, are hydrogen, halogen, a $C_1$-$C_{12}$ linear or branched alkyl group, a $C_1$-$C_{12}$ linear or branched alkoxy group, or a $C_6$-$C_{24}$ aryl or substituted aryl group;

X is a monovalent radical comprising a polymerization initiator moiety selected from the group consisting of phosphine oxide

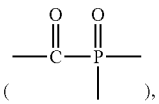

a peroxide group, an azide group, an α-hydroxyketone, or an α-aminoketone;

Y is a monovalent radical of formula (2)

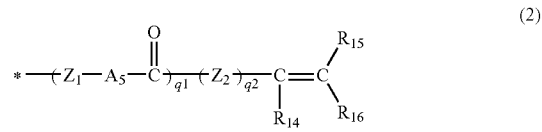

(2)

in which $Z_1$ and $Z_2$ independent of each other are a covalent bond, a linear or branched $C_1$-$C_{12}$ alkylene divalent radical, a linear or branched $C_1$-$C_{12}$ alkylene divalent radical having one or more hydroxyl groups, a radical of —($CH_2CH_2O$)$_d$—$CH_2CH_2$— in which d is an integer of 1 to 10, unsubstituted phenylene divalent radical, $C_1$-$C_4$ alkyl or $C_1$-$C_4$ alkoxy substituted phenylene divalent radical, $C_7$-$C_{12}$ aralkylene divalent radical,

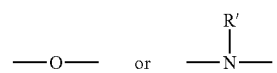

in which R' is H or $C_1$-$C_8$ alkyl; $A_5$ is a covalent bond,

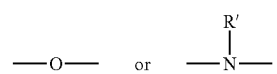

in which R' is H or $C_1$-$C_8$ alkyl; $q_1$ and $q_2$ independent of each other are an integer of 0 or 1; $R_{14}$ is hydrogen, $C_1$-$C_4$ alkyl or halogen; $R_{15}$ and $R_{16}$ independent of each other are hydrogen, $C_1$-$C_4$ alkyl, phenyl, carboxy, halogen, or a radical of

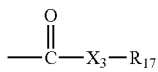

in which $X_3$ is

as defined above or —S— and $R_{17}$ is $C_1$-$C_{12}$ alkyl, $C_1$-$C_{12}$ hydroxyalkyl, $C_1$-$C_{12}$ aminoalkyl, alkylaminoalkyl having up to 12 carbon atoms, or dialkylaminoalkyl having up to 12 carbon atoms; and $L^1$ and $L^2$ independently of each other are a covalent bond or a linker; and b. curing the lens-forming material in the mold to form a UV-absorbing ophthalmic lens.

16. The method of claim 15, wherein the polymerization initiator moiety comprises a monovalent radical of formula IIa, IIb or XI

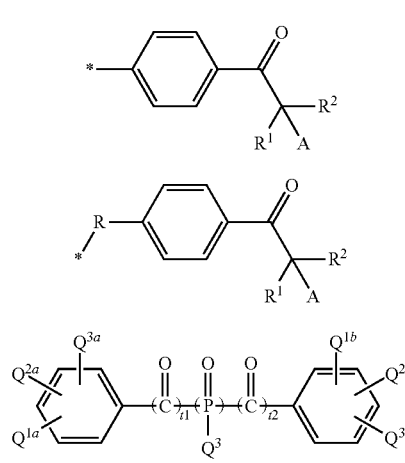

wherein:

(1) R is oxygen, nitrogen, a linear or branched $C_1$-$C_{12}$ alkylene divalent radical, a divalent radical of —OCH$_2$CH$_2$O—, a divalent radical of

in which $R^H$ is hydrogel or a $C_1$-$C_{12}$ alkyl radical and alk is $C_1$-$C_{12}$ alkylene divalent radical, or combinations thereof, $R^1$ and $R^2$ are, independently, hydrogen, a $C_1$-$C_{12}$ linear or branched alkyl group, a $C_6$-$C_{24}$ aryl or substituted aryl group, a $C_7$-$C_{24}$ aralkyl group;

(2) A is a monovalent radical selected from the group consisting of a hydroxyl group, a $C_1$-$C_{12}$ alkoxy group, a $C_6$-$C_{24}$ aryloxy group, a primary amino group, secondary amino group, and tertiary amino group; and (3) t1 and t2 independent of each other are 0 or 1 provided that at least one of t1 and t2 is 1, one of $Q^{1a}$ and $Q^{1b}$ is a covalent bond and the other is hydrogen, $C_1$-$C_6$ linear or branched alkyl group, or $C_1$-$C_6$ linear or branched alkoxy group, $Q^{2a}$, $Q^{2b}$, $Q^{3a}$, $Q^{3b}$ independently of one another hydrogen are $C_1$-$C_{12}$ linear or branched alkyl group, or $C_1$-$C_{12}$ linear or branched alkoxy group, wherein, in formula I, $L^1$ and $L^2$ independent of each other are a covalent bond or a divalent radical of

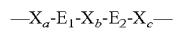

in which:

$X_a$ is a covalent bond, carbonyl

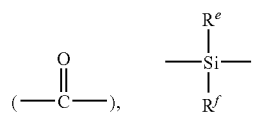

in which $R^e$ and $R^f$ independently of each other are a $C_1$-$C_8$-alkyl, phenyl or a $C_1$-$C_4$ alkyl- or $C_1$-$C_4$-alkoxy-substituted phenyl, a divalent radical of —($R^a$O)$_n$— in which $R^a$ is a linear or branched $C_1$-$C_{12}$-alkylene and n is from 1 to 10,

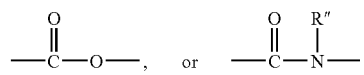

in which R" is H or $C_1$-$C_8$ alkyl;

$E_1$ and $E_2$ independently of each other are a covalent bond, a divalent radical of —($R^a$O)$_n$— in which $R^a$ and n are defined above,

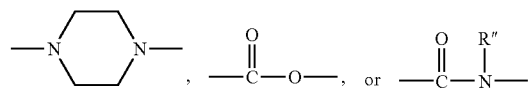

in which R" is H or $C_1$-$C_8$ alkyl, a $C_1$ to $C_{12}$ linear or branched alkylene divalent radical, a cycloalkyl diradical with up to 40 carbon atoms, an alkylcycloalkyl diradical with up to 40 carbon atoms, an alkylaryl diradical with up to 40 carbon atoms, an arylalkylene divalent radical with up to 40 carbon atoms, or a dicarbonyl group having the formula —C(O)$L^3$C(O)— in which $L^3$ is a $C_1$ to $C_{12}$ linear or branched alkylene divalent radical or —($R^{e1}$—O)$_{w1}$—($R^{e2}$—O)$_{w2}$—($R^{e3}$—O)$_{w3}$—, wherein $R^{e1}$, $R^{e2}$, and $R^{e3}$ independently of one another are a linear or branched $C_1$-$C_4$-alkylene and w1, w2 and w3 independently of one another are a number from 0 to 20 provided that the sum of (w1+w2+w3) is 1 to 60; and $X_b$ and $X_c$ independently of each other are a covalent bond,

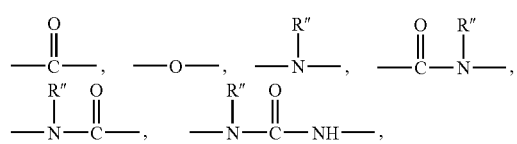

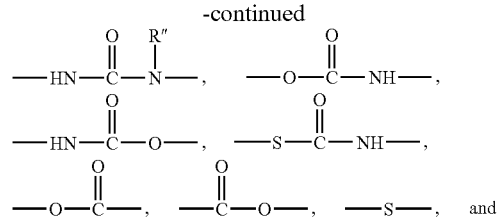 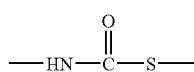
in which R″ is defined above.
* * * * *